(12) United States Patent
Bauer et al.

(10) Patent No.: US 11,649,247 B2
(45) Date of Patent: May 16, 2023

(54) 7-PHENYLETHYLAMINO-4H-PYRIMIDO [4,5-D][1,3]OXAZIN-2-ONE COMPOUNDS AS MUTANT IDH1 AND IDH2 INHIBITORS

(71) Applicant: Eli Lilly and Company, Indianapolis, IN (US)

(72) Inventors: Renato Alejandro Bauer, Indianapolis, IN (US); Serge Louis Boulet, Fishers, IN (US); Timothy Paul Burkholder, Carmel, IN (US); Patric James Hahn, Indianapolis, IN (US); Zoran Rankovic, Memphis, TN (US)

(73) Assignee: Eli Lilly and Company, Indianapolis, IN (US)

( * ) Notice: Subject to any disclaimer, the term of this patent is extended or adjusted under 35 U.S.C. 154(b) by 113 days.

(21) Appl. No.: 17/202,515

(22) Filed: Mar. 16, 2021

(65) Prior Publication Data

US 2021/0230185 A1    Jul. 29, 2021

Related U.S. Application Data

(63) Continuation of application No. 16/349,873, filed as application No. PCT/US2017/065246 on Dec. 8, 2017, now Pat. No. 11,001,596.

(60) Provisional application No. 62/435,283, filed on Dec. 16, 2016.

(51) Int. Cl.
  *C07D 498/04* (2006.01)
  *A61P 35/02* (2006.01)

(52) U.S. Cl.
  CPC ............ *C07D 498/04* (2013.01); *A61P 35/02* (2018.01)

(58) Field of Classification Search
  None
  See application file for complete search history.

(56) References Cited

FOREIGN PATENT DOCUMENTS

| WO | 2013/046136 A1 | 4/2013 |
|---|---|---|
| WO | 2016/171755 A1 | 10/2016 |
| WO | 2017/019429 A1 | 2/2017 |
| WO | 2017/213910 A1 | 12/2017 |

OTHER PUBLICATIONS

Written Opinion for PCT/US2017/065246 (dated Mar. 1, 2018).
International Search Report for PCT/US2017/065246 (dated Mar. 1, 2018).

*Primary Examiner* — Craig D Ricci
(74) *Attorney, Agent, or Firm* — Joseph Pletcher

(57) ABSTRACT

A compound, as defined herein, or pharmaceutical composition containing the compound, for use in treating IDH1 or IDH2 mutant cancer and having the structure: (I).

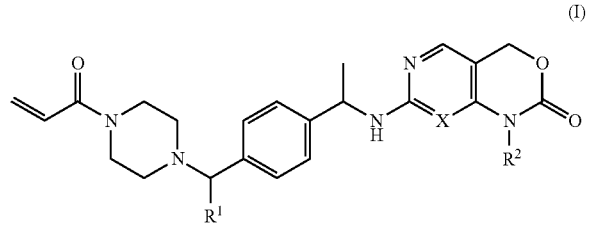

3 Claims, No Drawings

7-PHENYLETHYLAMINO-4H-PYRIMIDO [4,5-D][1,3]OXAZIN-2-ONE COMPOUNDS AS MUTANT IDH1 AND IDH2 INHIBITORS

The isocitrate dehydrogenase (IDH) protein is an important enzyme in the citric acid (tricarboxylic acid or Krebs) cycle. The citric acid cycle is centrally important to many biochemical pathways and is one of the earliest established components of cellular metabolism.

Isocitrate dehydrogenases catalyze the oxidative decarboxylation of isocitrate to α-ketoglutarate (2-oxoglutarate). These enzymes belong to two distinct subclasses, one of which utilizes nicotinamide adenine dinucleotide (NAD(+)) as the electron acceptor and the other nicotinamide adenine dinucleotide phosphate (NADP(+)). Three mammalian isocitrate dehydrogenases have been reported: one NAD(+)-dependent isocitrate dehydrogenase, a multisubunit enzyme which localizes to the mitochondrial matrix, and two NADP(+)-dependent isocitrate dehydrogenases, one of which is mitochondrial and the other predominantly cytosolic. Each NADP(+)-dependent isozyme is a dimer. The protein encoded by the IDH1 gene is the NADP(+)-dependent isocitrate dehydrogenase found in the cytoplasm and peroxisomes. The cytoplasmic enzyme serves a significant role in cytoplasmic NADPH production. IDH1 is expressed in a wide range of species and in organisms that lack a complete citric acid cycle.

Recently, mutations in IDH1, and the related isoform IDH2, have been found in several types of cancers. Mutations were found to occur at specific amino acids along the protein sequence and to be heterozygously expressed, consistent with a gain of function. These mutations occur at functionally conserved residues and biochemical studies of the mutant forms of IDH1 and IDH2 demonstrated a loss of normal function, the reversible conversion of isocitrate to α-ketoglutarate. The result of these mutations is to allow a new (or neomorphic) conversion of α-ketoglutarate (αKG) to 2-hydroxyglutarate (2HG). As a result, cancers cells that harbor mutant forms of IDH1 or IDH2 form substantially higher concentrations of 2HG. High levels of 2HG result in a block in cell differentiation that can be reversed by mutant IDH1 or IDH2 inhibition.

Application PCT/US2016/043264 discloses covalent inhibitors of mutant IDH1. There is a further need for compounds that selectively inhibit mutant IDH1 and IDH2 enzyme for the treatment of various cancers. There is a further need for compounds that selectively inhibit mutant IDH1 and IDH2 enzyme demonstrating neomorphic activity over wild type IDH1 and IDH2 for the treatment of various cancers. The present invention provides compounds of Formula I or Ia that are inhibitors of mutant IDH1 and IDH2. The compounds of Formula I or Ia are covalent inhibitors that selectively inhibit mutant IDH1 and IDH2.

One aspect of the invention is to provide mutant IDH1 and IDH2 enzyme inhibitor compounds of the Formula:

I

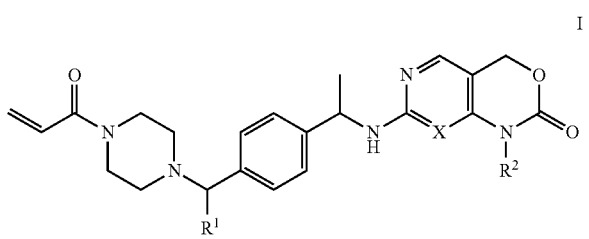

wherein:
$R^1$ is —$CH_2CH(CH_3)_2$, —$CH_2CH_3$, —$CH_2CH_2OCH_3$, or —$CH_2$-cyclopropyl;
$R^2$ is —$CH_3$ or —$CH_2CH_3$;
X is N or CH; or
a pharmaceutically acceptable salt thereof.

A further aspect of the invention is to provide mutant IDH1 and IDH2 enzyme inhibitor compounds of the Formula:

Ia

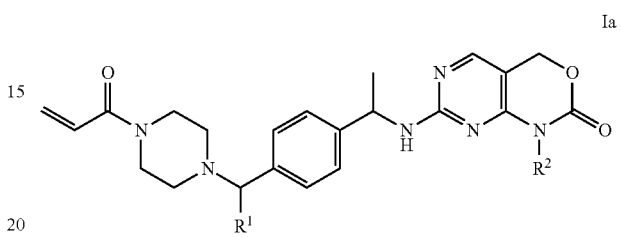

wherein
$R^1$ is —$CH_2CH(CH_3)_2$, —$CH_2CH_3$, —$CH_2CH_2OCH_3$, or —$CH_2$-cyclopropyl;
$R^2$ is —$CH_3$ or —$CH_2CH_3$; or
a pharmaceutically acceptable salt thereof.

A further aspect of the present invention provides a compound of Formula I or Ia which is:
7-[[(1S)-1-[4-[(1R)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one;
7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one;
1-Ethyl-7-[[(1S)-1-[4-[1-(4-prop-2-enoylpiperazin-1-yl)propyl]phenyl]ethyl]amino]-4H-pyrimido[4,5-d][1,3]oxazin-2-one, isomer 1;
1-Ethyl-7-[[(1S)-1-[4-[1-(4-prop-2-enoylpiperazin-1-yl)propyl]phenyl]ethyl]amino]-4H-pyrimido[4,5-d][1,3]oxazin-2-one, isomer 2;
or a pharmaceutically acceptable salt of any of them.

Another aspect of the present invention is a compound of Formula I or Ia which is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one or a pharmaceutically acceptable salt thereof.

Another aspect of the present invention provides a pharmaceutical composition comprising a mutant IDH1 inhibitor compound of Formula I or Ia, or a pharmaceutically acceptable salt thereof, and a pharmaceutically acceptable carrier.

A further aspect of the present invention provides a method of treating a cancer expressing mutant IDH1 or mutant IDH2 which is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma in a patient comprising administering to a patient in need thereof a therapeutically effective amount of a compound of Formula I or Ia, or a pharmaceutically acceptable salt thereof.

Another aspect of the present invention provides a method of treating a cancer expressing mutant IDH1 or mutant IDH2 which is fibrosarcoma, acute myeloid leukemia, glioma, or glioblastoma in a patient comprising administering to a patient in need thereof a therapeutically effective amount of a compound of Formula I or Ia, or a pharmaceutically acceptable salt thereof.

A further aspect of the present invention provides a compound of Formula I or Ia, or a pharmaceutically acceptable salt thereof, for use in therapy.

Another aspect of the present invention provides a compound of Formula I or Ia, or a pharmaceutically acceptable salt thereof, for use in the treatment of a cancer expressing mutant IDH1 or mutant IDH2 which is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma.

A further aspect of the present invention provides a compound of Formula I or Ia, or a pharmaceutically acceptable salt thereof, for use in the treatment of a cancer expressing mutant IDH1 or mutant IDH2 which is fibrosarcoma, acute myeloid leukemia, glioma, or glioblastoma.

Another aspect of the present invention provides use of a compound of Formula I or Ia, or a pharmaceutically acceptable salt thereof, for the manufacture of a medicament for the treatment of a cancer expressing mutant IDH1 or mutant IDH2 which is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma.

A further aspect of the present invention provides use of a compound of Formula I or Ia, or a pharmaceutically acceptable salt thereof, for the manufacture of a medicament for the treatment of a cancer expressing mutant IDH1 or mutant IDH2 which is fibrosarcoma, acute myeloid leukemia, glioma, or glioblastoma.

The term "patient" means mammal and "mammal" includes, but is not limited to, a human.

"Therapeutically effective amount" means the dosage of the compound of Formula I or Ia, or pharmaceutically acceptable salt thereof, or pharmaceutical composition containing the compound, or pharmaceutically acceptable salt thereof, necessary to inhibit mutant IDH1 or mutant IDH2 in a cancer patient, leading to the release of the block in differentiation with resulting inhibition of tumor cell growth and eliminate or slow or arrest the progression of the cancer in a patient. Anticipated dosages of a compound of Formula I or Ia, or a pharmaceutically acceptable salt thereof are in the range of 1 mg/patient/day to 2000 mg/patient/day. Preferred dosages are anticipated to be in the range of 5 mg/patient/day to 1800 mg/patient/day. Most preferred dosages are anticipated to be in the range of 40 mg/patient/day to 1600 mg/patient/day. The exact dosage required to treat a patient and the length of treatment time will be determined by a physician in view of the stage and severity of the disease as well as the specific needs and response of the individual patient. Although expressed as dosage on a per day basis, the dosing administration may be adjusted to provide a more optimal therapeutic benefit to a patient and to manage or ameliorate any drug related toxicities. In addition to daily dosing, twice a day (B.I.D.) dosing; three times a day (T.I.D.) dosing; dosing every other day (Q2D); every other day over a five day period followed by two days without dosing (T.I.W.); or every third day (Q3D) may be appropriate.

The terms "treatment," "treat," and "treating," are meant to include the full spectrum of intervention for the cancer from which the patient is suffering, such as administration of the active compound to alleviate, slow, or reverse one or more of the symptoms and to delay progression of the cancer even if the cancer is not actually eliminated.

The term —$CH_2CH(CH_3)_2$ means 2-methylpropyl, the term —$CH_2CH_2OCH_3$ means 2-methoxyethyl, and the term —$CH_2$-cyclopropyl means cyclopropylmethyl.

A compound of Formula I or Ia, or a pharmaceutically acceptable salt thereof, is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, for example, REMINGTON: THE SCIENCE AND PRACTICE OF PHARMACY, L. V. Allen, Editor, $22^{nd}$ Edition, Pharmaceutical Press, 2012.

In a particular embodiment, the pharmaceutical composition comprises 7-{[(1S)-1-(4-[(1S)-1-(4-acryloylpiperazin-1-yl)-2-cyclopropylethyl]phenyl]ethyl]amino}-1-ethyl-1,4-dihydro-2H-pyrimido[4,5-d][1,3]oxazin-2-one or a pharmaceutically acceptable salt thereof, together with a pharmaceutically acceptable carrier and optionally other therapeutic ingredients particularly for treatment of cancer generally or a specific cancer type.

A compound of Formula I or Ia, or a pharmaceutically acceptable salt, may be administered either simultaneously with, or before, or after, one or more other therapeutic agents. The compound of Formula I or Ia, or a pharmaceutically acceptable salt, when administered with one or more other therapeutic agents, may be administered separately, by the same or different route of administration, or together in the same pharmaceutical composition as the other therapeutic agent(s). Where one or more additional therapeutic agents are administered, the administration of each therapeutic agent may be simultaneous, separate, or sequential.

A compound of Formula I or Ia is capable of reaction with a number of inorganic and organic acids to form pharmaceutically acceptable acid addition salt. Such pharmaceutically acceptable salts and common methodology for preparing them are well known in the art. See, for example, P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

A compound of Formula I of Ia, or a pharmaceutically acceptable salt thereof, may be prepared by a variety of procedures known in the art, as well as those described below. The specific synthetic steps may be combined in a different order to prepare a compound of Formula I or Ia, or a pharmaceutically acceptable salt thereof.

Additionally, certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fifth Edition, by Peter G. M. Wuts and Theodora W. Greene, John Wiley and Sons, Inc. 2014).

Compounds of Formula I or Ia are named according to IUPAC, and may also be named according to CAS, and other names may be used to unambiguously identify a compound of Formula I or Ia, or a pharmaceutically acceptable salt thereof.

It will be understood a compound of Formula I or Ia may be depicted as a single stereoisomer. There are two chiral centers giving rise to four diastereomers. As used herein, references to a single stereoisomer are meant to also include stereoisomeric mixtures including the named or depicted compound of Formula I or Ia. Herein, the Cahn-Ingold-Prelog designations of (R)- and (S)- may be used to refer to specific stereoisomers. Specific stereoisomers can be prepared by stereospecific synthesis using enantiomerically pure or enriched starting materials. The specific stereoisomers of either starting materials, intermediates, or racemic mixtures including compounds of Formula I or Ia can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. For compounds of Formula I or Ia having a configuration with all stereocenters shown, "substantially enantiomerically pure" means the isomeric purity is greater than 90% enantiomeric excess. In another embodiment a compound of Formula I or Ia isomeric purity is greater than 95% enantiomeric excess. In still another embodiment a compound of Formula I or Ia isomeric purity is greater than 98% enantiomeric excess. In yet another embodiment a compound of Formula I or Ia isomeric purity is greater than 99% enantiomeric excess. All stereoisomers, individually and including diastereomeric mixtures of the compounds of Formula I or Ia are contemplated within the scope of the present invention. The designations "isomer 1" and "isomer 2" and "diastereomer 1" and "diastereomer 2" refer to the compounds that elute from chiral chromatography first and second, respectively, and if chiral chromatography is initiated early in the synthesis, the same designation is applied to subsequent intermediates and examples.

The compounds employed as initial starting materials in the synthesis of the compounds of Formula I or Ia are well known and, to the extent not commercially available, are readily synthesized using specific references provided, by standard procedures commonly employed by those of ordinary skill in the art or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Certain abbreviations are defined as follows: "ACN" means acetonitrile; "αKG" means Alpha-ketoglutarate or 2-ketoglutarate; "alloc" means allyloxycarbonyl; "ATCC" means American Type Culture collection; "BCA" means bicinchoninic acid; "BSA" means Bovine Serum Albumin; "CDI" means 1,1'-carbonyldiimidazole; "DCC" means 1,3-dicyclohexylcarbodiimide; "DCM" means dichloromethane; "DEAD" means diethyl azodicarboxylate; "DIAD" means diisopropyl azodicarboxylate; "DIC" means diisopropylcarbodiimide; "DIPEA" means diisopropylethylamine or N-ethyl-N-isopropyl-propan-2-amine; "DMAP" means dimethylaminopyridine; "DMF" means dimethylformamide; "DMSO" means dimethyl sulfoxide; "DTT" means dithiothreitol; "EDC" means EDAC, EDCI, or 1-(3-dimethylaminopropyl)-3-ethylcarbodiimide hydrochloride; "EDTA" means ethylenediaminetetraacetic acid; "EGTA" means ethylene glycol tetraacetic acid; "EtOAc" means ethyl acetate; "EtOH" means ethanol or ethyl alcohol; "Ex" means example; "HATU" means (dimethylamino)-N,N-dimethyl(3H-[1,2,3]triazolo[4,5-b]pyridin-3-yloxy)methaniminium hexafluorophosphate; "HBTU" means 2-(1H-benzotriazole-1-yl)-1,1,3,3-tetramethyluronium hexafluorophosphate; "2HG" means 2-hydroxyglutarate; "d$_5$-3HG" means 3-hydroxy-1,5-pentanedioic-2,2,3,4,4-d$_5$ acid; "HILIC" means hydrophilic interaction liquid chromatography; "HOAt" means 1-hydroxy-7-azobenzotriazole; "HOBt" means 1-hydroxylbenzotriazole hydrate; "HPLC" means high-performance liquid chromatography; "IC$_{50}$" means the concentration of an agent that produces 50% of the maximal inhibitory response possible for that agent; "mCPBA" means meta-chloroperbenzoic acid; "MeOH" means methanol or methyl alcohol; "NADP$^+$ and NADPH" means the oxidized and reduced forms of nicotinamide adenine dinucleotide phosphate respectively; "NMP" means N-methyl-2-pyrrolidone; "PG" means protecting group; "Prep" means preparation; "PyBOP" means benzotriazol-1-yloxytripyrrolidino-phosphonium hexafluorophosphate; "PyBrop" means bromo-tris-pyrrolidino phosphoniumhexafluoro phosphate; "rpm" means revolutions per minute; "(R)-RUCY®-XylBINAP" means RuCl[(R)-daipena][(R)-xylbinap]; "S$_N$Ar" means nucleophilic aromatic substitution; "TEA" means triethylamine; "TFA" means trifluoroacetic acid; "THF" means tetrahydrofuran; and "Tris" means tris(hydroxymethyl)aminomethane.

The compounds of Formula I or Ia, or pharmaceutically acceptable salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I or Ia, or pharmaceutically acceptable salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

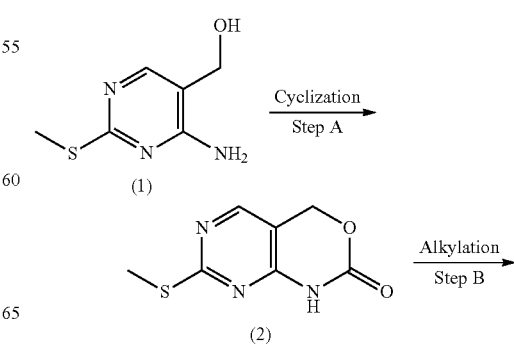

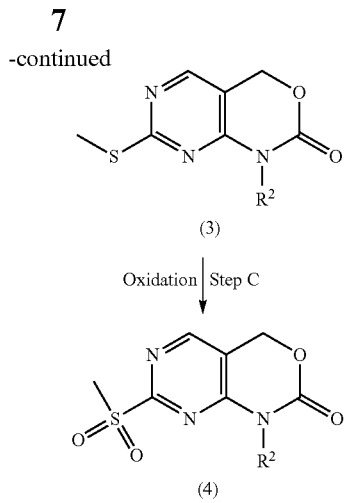

In Scheme 1, a series of reactions leads to a 1-substituted-7-(methylsulfonyl)-1,4-dihydro-2H-pyrimido[4,5-d][1,3]oxazin-2-one, (4), the product of Step C where $R^2$ is as previously defined. "PG" is a protecting group developed for the amino group or oxygen group such as for carbamates, amides or esters. For example, 5-hydroxy methyl 4-amino-2-methylsulfanyl-pyrimidine can be cyclized under standard carbamoylation conditions to the oxazine-2-one using triphosgene and an organic base such as DIPEA or TEA at a temperature of about −30 to −35° C. to give Compound (2), the product of Step A. Alternatively a dihalide carbonyl or a di-pseudohalide carbonyl such as CDI, phosgene, or diphosgene can be used instead of triphosgene to complete the carbamoylation. The amine of the oxazine can be alkylated with the appropriate substituted alkyl halide such as an iodo reagent in a solvent such as NMP and an inorganic base such as $K_2CO_3$ at a temperature of about 50-65° C. to give Compound (3), the product of Step B. Alternatively, a Mitsunobu reaction can be accomplished to alkylate the amine of the oxazine using an appropriate alcohol such as MeOH. Mitsunobu reactions are well known in the art and can convert a hydroxyl group into a leaving group that is displaced by a wide variety of nucleophiles such as a carbamate using triphenylphosphine and an azodicarboxylate such as DIAD or DEAD in a solvent such as THF to give Compound (3). The sulfide can be oxidized to the sulfone under conditions well known in the art such as mCPBA or potassium peroxymonosulfate at a temperature of about 10 to 25° C. in a solvent such as ACN or DCM to give Compound (4), the product of Step C.

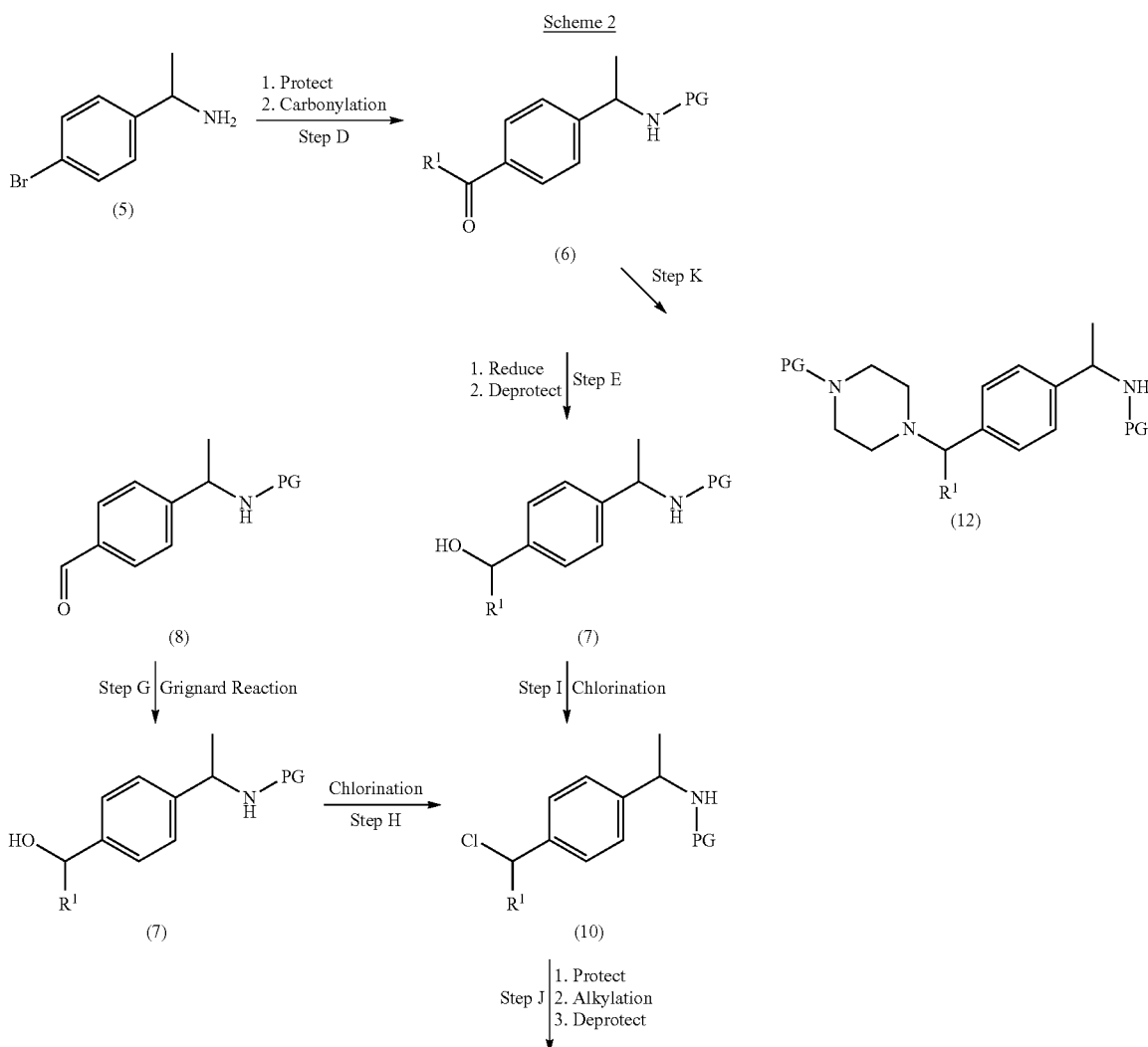

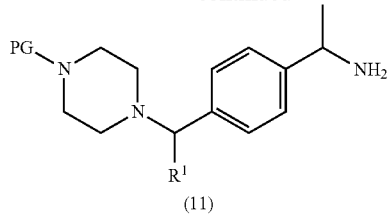

PG = protecting group or H

In Scheme 2, a (4-(1-aminoethyl)phenyl)methanol (7) can be generated over several steps from an aryl halide such as a bromide (5) using procedures well known to the skilled artisan. The amine can be protected in substep 1, Step D, where "PG" is a protecting group developed for the amino group such as an amide. The protected aryl bromide (5) can be converted to a ketone under lithium carbonylation conditions to give the aryl ketone (6) in substep 2, Step D. The ketone can then be reduced using a reducing agent such as sodium borohydride in a solvent such as MeOH in substep 1, Step E. The amine can be deprotected at this step (substep 2, Step E) or at a later point in the synthesis to give Compound (7). Alternatively, Compound (6) can be directly converted to Compound (12) in a reductive amination using titanium(IV) isopropoxide in a solvent such as THF and with heating to about 60° C. followed by cooling and the addition of MeOH and a reducing agent such as sodium cyanoborohydride to give Compound (12). Compound (7) can be converted to a benzyl halide such as a chloride under standard halogenation conditions using a halogenating agent such as thionyl chloride or $POCl_3$ in a solvent such as DCM to give compound (10), Step I. Compound (10) can be protected if needed and alkylated in Step J. For example, the amine, (10) can be protected in substep 1 of Step J using a protecting group such as a trifluoroacetyl or CBZ. Such protecting groups are well known and appreciated in the art. Alternatively, Compound 10 can be prepared from an aldehyde, Compound (8). Compound (8) can be prepared by oxidation of the corresponding benzyl alcohol under such conditions as Dess-Martin periodinane in a solvent such as DCM to give an aldehyde (8). A Grignard reaction can be accomplished in Step G on the aldehyde to give Compound (7). Compound (7) from Step G can be chlorinated in Step H to give Compound (10) as discussed above for Step I. The chloride of Compound (10) can be displaced with a mono-protected piperazine in a two-step, one pot procedure. It is not always necessary to protect the 1-phenylethylamine but if protection is chosen, it is advantageous to use a different protecting group on the 1-phenylethylamine than the piperazine amine product (11), Step J, substep 1, to selectively deprotect one or the other PG at the desired step. For example, the 1-phenylethylamine can be reacted with trifluoroacetic anhydride using an organic base such as TEA in a solvent such as DCM at a temperature of about 0-5° C. to give the protected amine product of substep 1, Step J. One skilled in the art would understand other protecting groups can be utilized on the amine such as CBZ. Displacement of the chloride can then be accomplished under conditions well known by one skilled in the art. For example, the halide can be displaced by the protected or unprotected piperazine using an inorganic base such as $K_2CO_3$ and utilizing KI, or NaI as a nucleophilic catalyst to accelerate the reaction. The mixture can be heated to about 60-80° C. in a solvent such as ACN to give the protected Compound (11) of substep 2, Step J. The protecting group on the 1-phenylethylamine can be removed with a base such as aqueous potassium hydroxide to give Compound (11) of substep 3, Step J.

Scheme 3

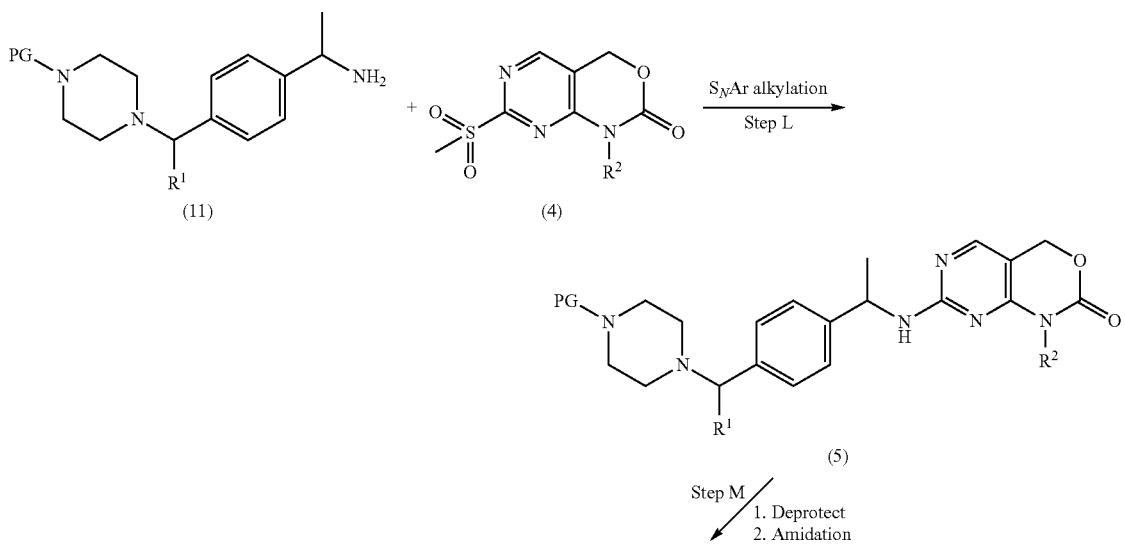

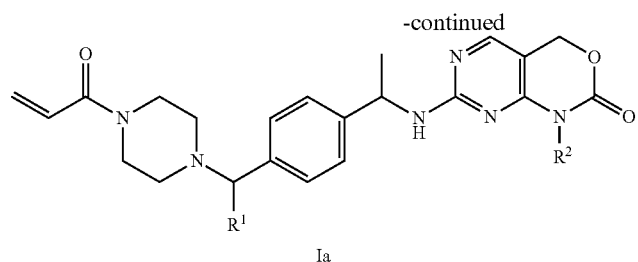

Ia

In Scheme 3, Compound (11) can be reacted with Compound (4), Scheme 1, in a $S_NAr$ reaction using an organic base such as DIPEA, CsF to accelerate the reaction, a solvent such as DMSO, and a temperature of about 70-80° C. to give the product of Step L. In Step M, substep 1, a tert-butoxy protected piperazine can be deprotected using an acid such as HCl in dioxane and MeOH or TFA in DCM whereas an alloc protected piperazine can be deprotected in the presence of a palladium source such as catalytic tetrakis (triphenylphosphine)palladium(0) in a solvent such as THF using a soft nucleophile such as dimedone to give the deprotected piperazine of substep 1, Step M. In substep 2, Step M, the piperazine can be amidated with acryloyl chloride at a temperature of about −50 to −78° C. with or without an organic base such as TEA if the amine is an acid salt in a solvent such as DCM to give compounds of Formula Ia. Alternatively, an amide coupling can be accomplished with acrylic acid and the appropriate amine in a solvent such as DMF with a coupling reagent such as EDC and an additive such as HOBt. One skilled in the art will recognize that there are a number of methods and reagents for amide formation resulting from the reaction of carboxylic acids and amines. For example, the reaction of the appropriate amine and acrylic acid in the presence of a coupling reagent with or without an organic base such as DIPEA or TEA can provide a compound of Formula Ia. Other coupling reagents include carbodiimides, such as DCC, DIC, or a carbonyldiimidazole such as CDI. Other amide coupling additives, such as HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as DMAP may be used to accelerate the desired amidation reaction.

Scheme 4

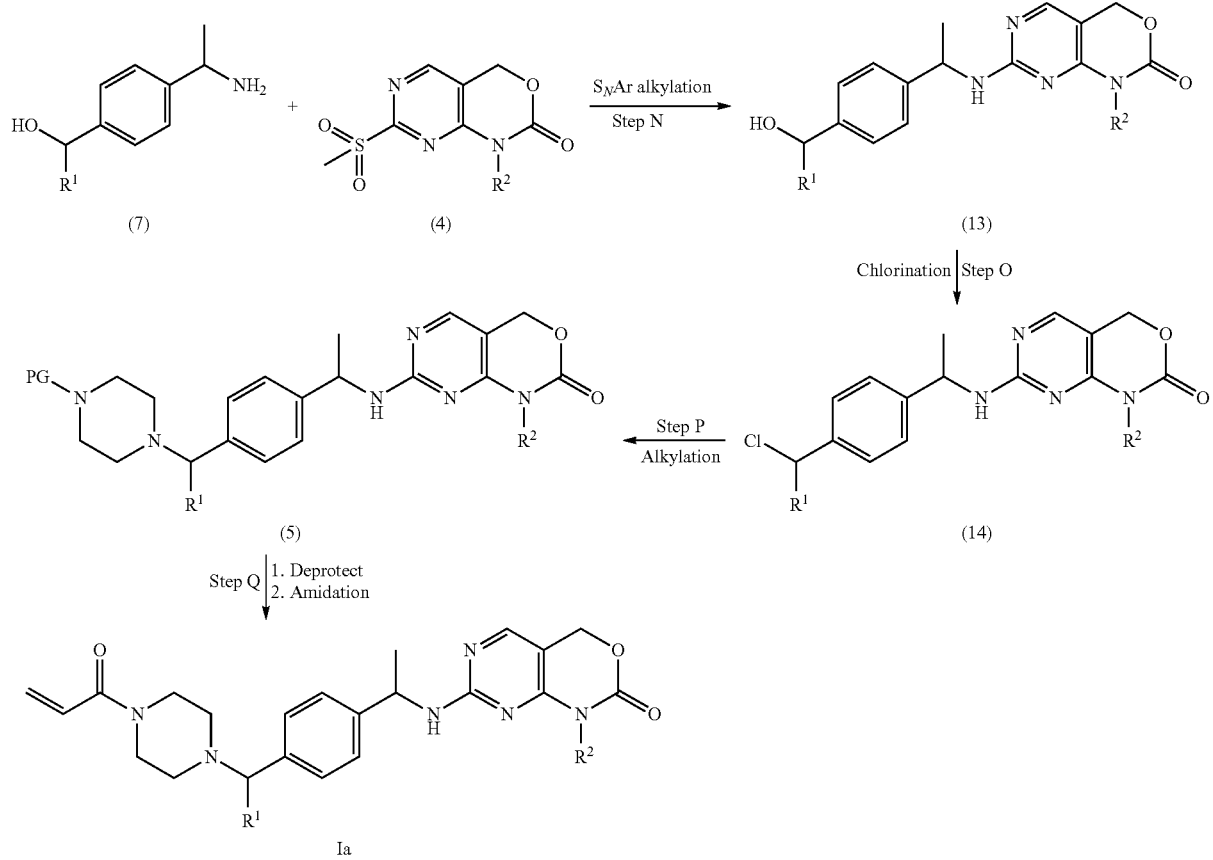

Alternatively in Scheme 4, the amine of the deprotected product of Compound (7), Scheme 2 can be reacted with Compound (4) as described in Scheme 3, Step L in a $S_NAr$ alkylation to give Compound 13. The hydroxyl can be chlorinated as described in Step I, Scheme 2 to give Compound 14, Step O. The chlorine of Compound (14) can be displaced in an alkylation with the piperazine as described in Scheme 2, Step 11, substep 2 to give Compound (5). The protected piperazine can be deprotected and the piperazine then amidated as described in Scheme 3, Step M to give compounds of Formula Ia.

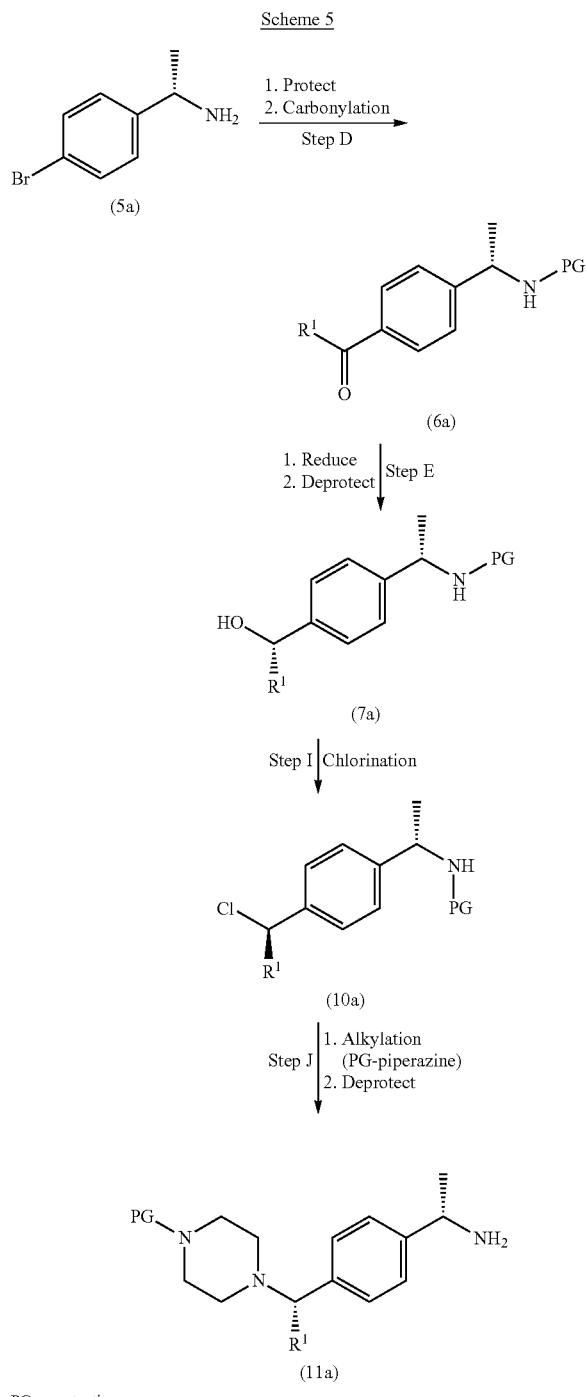

PG = protecting group

In scheme 5, a chiral (4-(1-aminoethyl)phenyl)methanol (7a) can be generated over several steps from a chiral aryl halide such as a bromide (5a) using procedures well known to the skilled artisan. The amine can be protected in substep 1, Step D, where "PG" is a protecting group developed for the amino group such as an amide. The aryl bromide (5a) can be converted to a ketone under lithium carbonylation conditions to give the aryl ketone (6a) in substep 2, Step D. The ketone can then be asymmetrically reduced using a chiral reducing agent such as (R)-RUCY-XylBINAP in a solvent such as EtOH to provide compound 7a in substep 1, Step E. Compound (7a) can be converted to a chiral benzyl halide such as a chloride under standard halogenation conditions using a halogenating agent such as benzoyl chloride in a solvent such as t-butyl ether to give compound (10a), Step I. Compound (10a) is first reacted with a protected piperazine (PG-piperazine) in the presence of a base such as sodium bicarbonate in a solvent such as acetonitrile to give a protected form in substep 1, Step J. The protected form is then deprotected with a base such as aqueous potassium hydroxide in a solvent such as EtOH to provide compound (11a), substep 2, Step J.

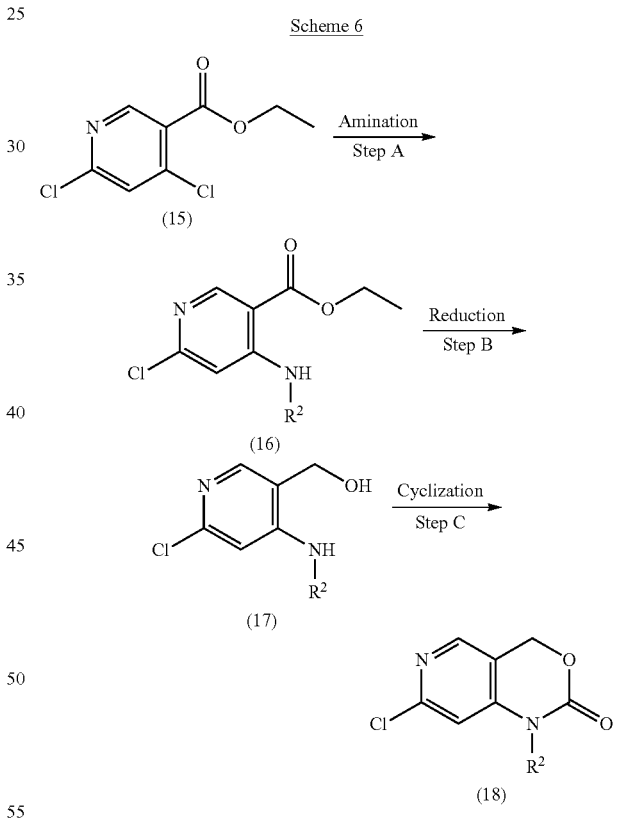

In Scheme 6, a series of reactions leads to a 1-substituted-7-chloro-4H-pyrido[4,3-d][1,3]oxazin-2-one (18), the product of Step C where $R^2$ is as previously defined. For example, ethyl 4,6-dichloropyridine-3-carboxylate (15) can be reacted with an amine under standard conditions to give the 6-chloro-4-(amino)pyridine-3-carboxylate (16) in a solvent such as acetonitrile. Reduction of the ester group in Compound (16) using a hydride reagent such as lithium aluminum hydride in a solvent such as THF affords the (4-amino-6-chloro-3-pyridyl)methanol (17). Compound such as 17 can be cyclized under standard carbamoylation conditions to the oxazine-2-one using triphosgene and an organic base such as DIPEA or TEA at a temperature of about −20° C. to give Compound (18), the product of Step C. Alternatively a dihalide carbonyl or a di-pseudohalide carbonyl such as CDI, phosgene, or diphosgene can be used instead of triphosgene to complete the carbamoylation. Compound 11, prepared as shown above in Schemes 2 or 5, or as described in alternatives to either Scheme, may be reacted with Compound 18 under standard alkylating conditions. The resulting intermediate compound is then deprotected and amidated as described above in Schemes 3 or 4 to afford the compounds of Formula I where X is CH.

In an optional step, a pharmaceutically acceptable salt of a compound of Formula I or Ia can be formed by reaction of an appropriate free base of Formula I or Ia with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I or Ia is readily converted to and may be isolated as a pharmaceutically acceptable salt.

PREPARATION 1

7-Methylsulfanyl-1,4-dihydropyrimido[4,5-d][1,3]oxazin-2-one

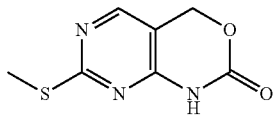

Triphosgene (859 g, 2.9 mol) is added to a solution of (4-amino-2-methylsulfanyl-pyrimidin-5-yl)methanol (900 g, 5.26 mol) in THF (22.5 L) over 15 minutes at −30° C. DIPEA (2.449 g, 18.92 mol) is added over 1 hour, while maintaining the reaction temperature between −35 and −30° C. The reaction mixture is then poured over ice water (30 L) and 2-methyltetrahydrofuran (10 L) is added. The organic phase is washed with water and brine. The organic phase is dried over $Na_2SO_4$ and is concentrated to dryness. The crude product is slurried with petroleum ether/EtOAc (1:1), filtered, and concentrated to give a yellow solid which is carried on without further purification (890.5 g, 1.62 mol, 83% purity, 86% yield). MS (m/z): 198 (M+H).

PREPARATION 2

1-Ethyl-7-(methylthio)-1,4-dihydro-2H-pyrimido[4,5-d][1,3]oxazin-2-one

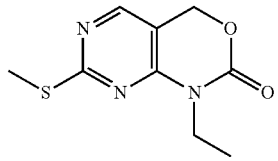

To a solution of 7-methyl sulfanyl-1,4-dihydropyrimido[4,5-d][1,3]oxazin-2-one (280 g, 1.42 mol) in NMP (2.24 L) is added $K_2CO_3$ (294.2 g, 2.13 mol) and ethyl iodide (336.3 g, 1.99 mol) at room temperature. The mixture is stirred for 16 hours at 50° C. and then diluted with DCM (3 L) and water (6 L). The organic phase is separated and washed with water and brine and concentrated to dryness to give the crude title compound (286 g, 1.27 mol, 83% purity, 91% yield). MS (m/z): 226 (M+H).

PREPARATION 3

1-Methyl-7-methylsulfanyl-4H-pyrimido[4,5-d][1,3]oxazin-2-one

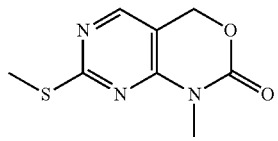

To a solution of triphenylphosphine (1.61 g, 6.08 mmol) and 7-methylsulfanyl-1,4-dihydropyrimido[4,5-d][1,3]oxazin-2-one (1.00 g, 5.07 mmol) in THF (25 mL) is added MeOH (0.248 mL, 6.08 mmol) followed by dropwise addition of DIAD (1.21 mL, 6.08 mmol) at ambient temperature. After stirring overnight the solvent is removed under vacuum and the resulting yellow oil is purified by silica gel chromatography (40-50% EtOAc/hexanes) to give the title compound as a white solid (1.08 g, 5.11 mmol, quantitative). MS (m/z): 212 (M+H).

PREPARATION 4

1-Ethyl-7-(methylsulfonyl)-1,4-dihydro-2H-pyrimido[4,5-d][1,3]oxazin-2-one

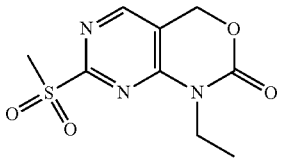 [SMILES: CCN1C(=O)OCc2cnc(S(C)(=O)=O)nc21]

To a stirred solution of 1-ethyl-7-(methylthio)-1,4-dihydro-2H-pyrimido[4,5-d][1,3]oxazin-2-one (286 g, 1.24 mol) in ACN (2.8 L) and water (1.4 L) is added potassium peroxymonosulfate (1526 g, 2.48 mol) as a solid over 20 minutes, and the resulting mixture is stirred for 16 hours at 10-20° C. The reaction mixture is filtered and the obtained filter cake is washed with DCM. The combined filtrate and DCM are washed with 5% $Na_2SO_3$, water, and brine. The organic phase is dried over $Na_2SO_4$ and concentrated to provide the title compound (133.8 g, 93% purity, 41% yield). MS (m/z): 258 (M+H).

The following compound is prepared essentially by the method of Preparation 4.

TABLE 1

| Prep. No. | Chemical name | Structure | ES/MS (m/z) (M + H) |
|---|---|---|---|
| 5 | 1-Methyl-7-methylsulfonyl-4H-pyrimido[4,5-d][1,3]oxazin-2-one | 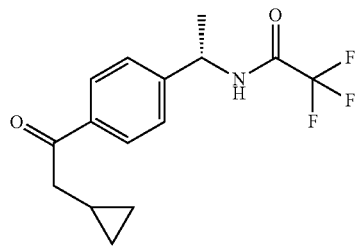 | 244 |

PREPARATION 6

N-[(1S)-1-(4-Bromophenyl)ethyl]-2,2,2-trifluoro-acetamide

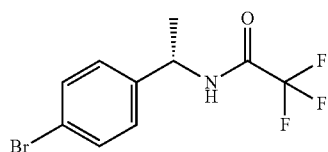 [SMILES: C[C@H](NC(=O)C(F)(F)F)c1ccc(Br)cc1]

Trifluoroacetic anhydride (165 mL, 1.17 mol) is added dropwise to a solution of (1S)-1-(4-bromophenyl)ethanamine (213 g, 1.06 mol) in ACN (1.3 L) at 5° C. followed by the dropwise addition of TEA (326 mL, 2.34 mol) over 1 hour. After 30 minutes, water (3 L) and brine (1 L) are added resulting in the formation of a colorless precipitate. The slurry is stirred for 15 minutes and then the solid is filtered, washed with water and hexanes, and dried by air current followed by drying at 40° C. under vacuum to give the title compound (290 g, 92%). $^1$H NMR ($d_6$-DMSO) δ 1.44 (d, 3H, J=7.1 Hz), 4.98 (dddd, 1H, J=7.6, 7.1, 7.1, 7.1 Hz), 7.30 (d, 2H, J=8.4 Hz), 7.55 (d, 2H, J=8.4 Hz), 9.91 (d, 1H, J=7.6 Hz).

PREPARATION 7

N-[(1S)-1-[4-(2-Cyclopropylacetyl)phenyl]ethyl]-2,2,2-trifluoro-acetamide n-Butyl lithium (2.5 M in hexanes, 53 mL, 130 mmol) is added dropwise to a solution of N-[(1S)-1-(4-bromophenyl)ethyl]-2,2,2-trifluoro-acetamide (18.00 g, 60.79 mmol) in THF (600 mL) at −78° C. so as to maintain an internal temperature below −70° C. After the addition is complete, the mixture is stirred for 45 minutes at −78° C. and then 2-cyclopropyl-N-methoxy-N-methyl-acetamide (11.4 g, 79.6 mmol) is added as a solution in THF (10 mL). The mixture is stirred at −78° C. for 45 minutes, saturated aqueous ammonium chloride is added, and the mixture is warmed to room temperature. The layers are separated and the organic layer is dried over anhydrous sodium sulfate, filtered, and concentrated under reduced pressure. To the solid is added a small amount of DCM and the mixture is heated briefly to dissolve the solids. The mixture is concentrated until just before precipitation and then hexanes (150 mL) is added dropwise with vigorous stirring to give a colorless solid. The solid is collected via filtration, washed with a small amount of hexanes, and dried under reduced pressure to give the title compound (13.82 g, 76%) as a colorless solid. MS (m/z): 298.3 (M−H).

The following compound is prepared essentially by the method of Preparation 7.

TABLE 2

| Prep. No. | Chemical name | Structure | ES/MS (m/z) (M + H) |
|---|---|---|---|
| 8 | 2,2,2-Trifluoro-N-[(1S)-1-[4-(3-methoxypropanoyl)phenyl]ethyl]acetamide, | 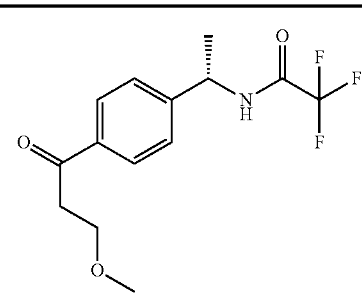 | 304 |

PREPARATION 9

1-[4-[(1S)-1-Aminoethyl]phenyl]-2-cyclopropyl-ethanol

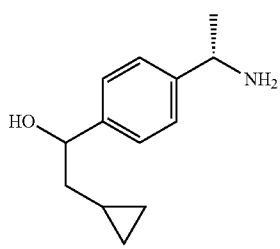

Sodium borohydride (0.1411 g, 2 equiv., 3.729 mmol,) is added to a solution of N-[(1S)-1-[4-(2-cyclopropylacetyl)phenyl]ethyl]-2,2,2-trifluoro-acetamide (558 mg, 1.86 mmol) in MeOH (15 mL) cooled in an ice water bath. The mixture is stirred for about 2.5 hours, and then potassium hydroxide (800 mg, 14.2 mmol) in water (3 mL) is added. The mixture is stirred at room temperature for about 20 hours. The mixture is concentrated and partitioned between DCM and water. The organic layer is washed with saturated aqueous sodium chloride, dried over sodium sulfate, filtered, and concentrated to give the title compound (354 mg, 1.38 mmol, 74%) as a white solid. The material is used without further purification. ES/MS (m/z): 189.0 (M−OH).

PREPARATION 10

2,2,2-Trifluoro-N-[(1S)-1-(4-formylphenyl)ethyl]acetamide

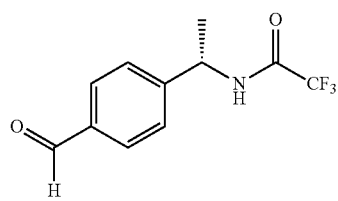 [SMILES: C[C@H](NC(=O)C(F)(F)F)c1ccc(C=O)cc1]

Dess-Martin periodinane (20.9 g, 49.3 mmol) is added to a 0° C. solution of 2,2,2-trifluoro-N-[(1S)-1-[4-(hydroxymethyl)phenyl]ethyl]acetamide (11.1 g, 44.9 mmol) in DCM (450 mL). The reaction mixture is stirred overnight and allowed to warm to room temperature. The reaction mixture is diluted with additional DCM and washed with saturated aqueous NaHCO₃, saturated aqueous Na₂S₂O₃, and brine. The combined organics are dried (Na₂SO₄), filtered, and concentrated to give a residue which is purified by silica gel chromatography eluting with a gradient of 0-50% EtOAc/hexanes to give the title compound as a white solid (9.5 g, 39 mmol, 86%). ES/MS (m/z): 244 (M−H).

PREPARATION 10a 2,2,2-Trifluoro-N-[(1S)-1-[4-(hydroxymethyl)phenyl]ethyl]acetamide

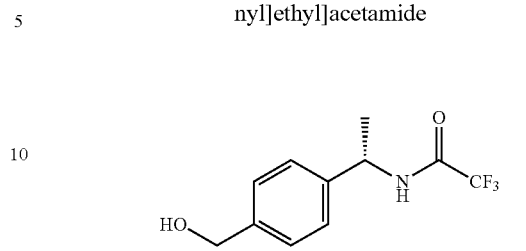

Trifluoroacetic anhydride (12 mL, 85.4 mmol) is added to a 0° C. solution of [4-[(1S)-1-aminoethyl]phenyl]methanol (10.8 g, 71.4 mmol) in CH₂Cl₂ (150 mL). After 10 minutes, triethylamine (24 mL, 172 mmol) in CH₂Cl₂ (8 mL) is added dropwise over 30 minutes, the cooling bath is removed and the reaction is stirred overnight. The reaction mixture is concentrated under vacuum, diluted with additional CH₂Cl₂, and washed with 1 N aqueous HCl and water. The organic phase is dried (Na₂SO₄), filtered, and concentrated. The crude material is purified by silica gel chromatography eluting with a gradient of 0-50% EtOAc/hexanes to give the title compound as a white solid (11.1 g, 44.9 mmol, 63%). ES/MS (m/z): 246 (M−H).

PREPARATION 11

2,2,2-Trifluoro-N-[(1S)-1-[4-(1-hydroxy-3-methyl-butyl)phenyl]ethyl]acetamide

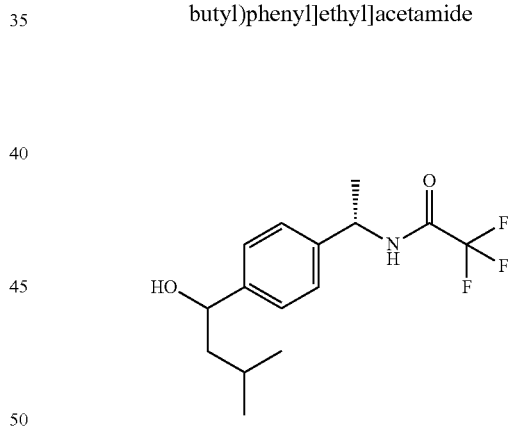

To a solution of 2,2,2-trifluoro-N-[(1S)-1-(4-formylphenyl)ethyl]acetamide (1.72 g, 7.01 mmol) in THF (35 mL) cooled in an ice water bath is added isobutylmagnesium bromide (2 M in diethyl ether, 7.0 mL, 14.0 mmol) and stirred for about 30 minutes. The mixture is quenched with saturated aqueous ammonium chloride and partitioned between EtOAc and water. The organic layer is washed with saturated aqueous sodium chloride, dried over sodium sulfate, filtered, and concentrated to give the title compound as an oil (1.40 g, 4.15 mmol, 59%) which is used without further purification. ES/MS (m/z): 302.0 (M−H).

The following compound is prepared essentially by the method of Preparation 11.

TABLE 3

| Prep. No. | Chemical name | Structure | ES/MS (m/z) (M + H) |
|---|---|---|---|
| 12 | 2,2,2-trifluoro-N-[(1S)-1-[4-(1-hydroxypropyl)phenyl]ethyl]acetamide | 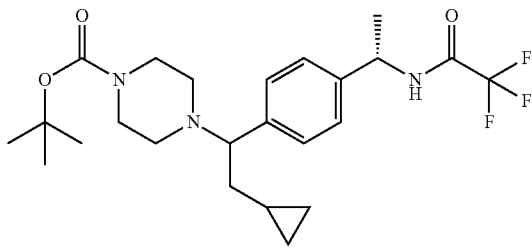 [SMILES: C[C@H](NC(=O)C(F)(F)F)c1ccc(C(CC2CC2)N2CCN(C(=O)OC(C)(C)C)CC2)cc1] | 293 (M + NH$_4$) |

PREPARATION 13 tert-Butyl 4-[2-cyclopropyl-1-[4-[(1S)-1-[(2,2,2-trifluoroacetyl)amino]ethyl]phenyl]ethyl]piperazine-1-carboxylate

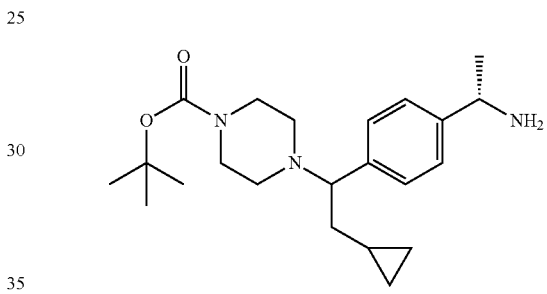

Titanium(IV) isopropoxide (60 mL, 200 mmol) is added to a solution of N-[(1S)-1-[4-(2-cyclopropylacetyl)phenyl]ethyl]-2,2,2-trifluoro-acetamide (12.0 g, 40.1 mmol) and tert-butyl piperazine-1-carboxylate (17.9 g, 96.1 mmol) in THF (80 mL) and the mixture is stirred at 60° C. overnight. The mixture is cooled to room temperature and MeOH (80 mL) is added followed by the portion-wise addition of sodium cyanoborohydride (5.3 g, 80 mmol). The mixture is stirred at room temperature for 8 hours and then water and MeOH are added and the mixture is stirred at room temperature overnight. The mixture is filtered to remove solids and the solids are rinsed with MeOH and water. The filtrate is partially concentrated to remove most of the MeOH and the residue is extracted with EtOAc (2×). The combined organic extracts are dried over anhydrous sodium sulfate, filtered, and concentrated under reduced pressure. The crude material is purified via column chromatography eluting with a gradient of 0% to 30% EtOAc in solvent B where solvent B is 1:1 hexanes:DCM to give the title compound (10.5 g, 56%) as a colorless solid. MS (m/z): 470.3 (M+H).

PREPARATION 14 tert-Butyl 4-[1-[4-[(1S)-1-aminoethyl]phenyl]-2-cyclopropyl-ethyl]piperazine-1-carboxylate Aqueous potassium hydroxide (5 M, 69 mL, 350 mmol) is added to a solution of tert-butyl 4-[2-cyclopropyl-1-[4-[(1S)-1-[(2,2,2-trifluoroacetyl)amino]ethyl]phenyl]ethyl]piperazine-1-carboxylate (32.24 g, 68.67 mmol) in EtOH (350 mL) and the resulting mixture is stirred at room temperature for 4 hours. The EtOH is removed under reduced pressure and to the residue is added saturated aqueous sodium bicarbonate and the mixture is extracted with DCM. The combined organic extracts are dried over anhydrous sodium sulfate, filtered, and concentrated under reduced pressure to give the title compound (24.33 g, 96.5% purity containing 3.5% residual DCM, 92% yield) as a colorless viscous oil. MS (m/z): 374.3 (M+H).

The following compound is prepared essentially by the method of Preparation 14.

TABLE 4

| Prep. No. | Chemical name | Structure | ES/MS (m/z) (M + H) |
|---|---|---|---|
| 15 | tert-Butyl 4-[1-[4-[(1S)-1-aminoethyl]phenyl]-3-methyl-butyl]piperazine-1-carboxylate | 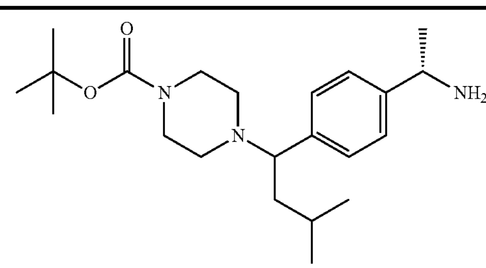 | 376 |

TABLE 4-continued

| Prep. No. | Chemical name | Structure | ES/MS (m/z) (M + H) |
|---|---|---|---|
| 16 | tert-Butyl 4-[(1R)-1-[4-[(1S)-1-aminoethyl]phenyl]propyl]piperazine-1-carboxylate, isomer 1 | 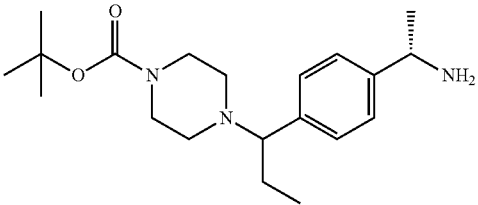 [SMILES: CCC(c1ccc([C@H](C)N)cc1)N1CCN(C(=O)OC(C)(C)C)CC1] | 348 |
| 17 | tert-Butyl 4-[(1R)-1-[4-[(1S)-1-aminoethyl]phenyl]propyl]piperazine-1-carboxylate, isomer 2 | 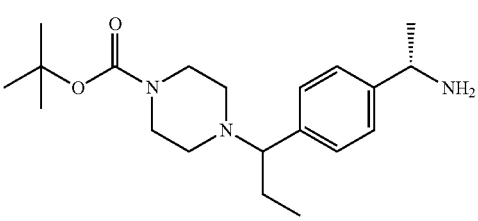 [SMILES: CCC(c1ccc([C@H](C)N)cc1)N1CCN(C(=O)OC(C)(C)C)CC1] | 348 |

ALTERNATE PREPARATION 14

A solution of potassium hydroxide (1.28 g, 22.9 mmol) in water (4 mL) is added to a solution of tert-butyl 4-[2-cyclopropyl-1-[4-[(1s)-1-[(2,2,2-trifluoroacetyl)amino]ethyl]phenyl]ethyl]piperazine-1-carboxylate (2.15 g, 4.58 mmol) in EtOH (23 mL) and the mixture stirred at room temperature. After about 6 hours, the mixture is concentrated. The residue is partitioned between DCM and saturated sodium bicarbonate solution. The organic layer is washed with water and saturated aqueous sodium chloride, dried over sodium sulfate, filtered, and concentrated to give the title compound as an oil which is used without purification (1.73 g, 4.49 mmol, 98%). ES/MS (m/z): 374.2 (M+H).

PREPARATION 18 tert-Butyl 4-[(1R)-1-[4-[(1S)-1-aminoethyl]phenyl]-2-cyclopropyl-ethyl]piperazine-1-carboxylate, diastereomer 1

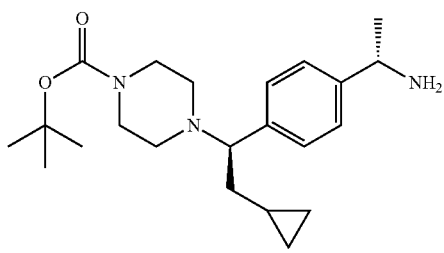 [SMILES: C[C@H](N)c1ccc([C@@H](CC2CC2)N2CCN(C(=O)OC(C)(C)C)CC2)cc1]

PREPARATION 19 tert-Butyl 4-[(1S)-1-[4-[(1S)-1-aminoethyl]phenyl]-2-cyclopropyl-ethyl]piperazine-1-carboxylate, diastereomer 2

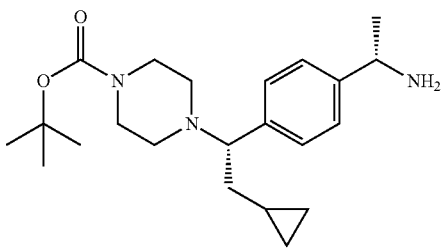 [SMILES: C[C@H](N)c1ccc([C@H](CC2CC2)N2CCN(C(=O)OC(C)(C)C)CC2)cc1]

A 1:1 mixture of tert-butyl 4-[(1R)-1-[4-[(1S)-1-aminoethyl]phenyl]-2-cyclopropyl-ethyl]piperazine-1-carboxylate, diastereomer 1 and tert-butyl 4-[(1S)-1-[4-[(1S)-1-aminoethyl]phenyl]-2-cyclopropyl-ethyl]piperazine-1-carboxylate, diastereomer 2 (3.23 g) is dissolved in MeOH (40 mL) and is separated into individual diastereomers by preparative chiral HPLC chromatography using the following conditions: column Chiralpak AD, 20 μm, (8×33 cm); injection volume 10 mL; eluent 100% MeOH with 0.2% DMEA; detection wavelength 220 nm; flow rate 400 mL/min. Preparation 12, tert-butyl 4-[(1R)-1-[4-[(1S)-1-aminoethyl]phenyl]-2-cyclopropyl-ethyl]piperazine-1-carboxylate, diastereomer 1, is obtained from the first eluting peak as a clear viscous oil (1.50 g, 46%, >99% de). MS (m/z): 374.3 (M+H). Preparation 13, tert-butyl 4-[(1S)-1-[4-[(1S)-1-aminoethyl]phenyl]-2-cyclopropyl-ethyl]piperazine-1-carboxylate, diastereomer 2, is obtained from the second eluting peak as a clear viscous oil (1.46 g, 45%, >98.2% de). MS (m/z): 374.3 (M+H).

PREPARATION 20

N,3-Dimethoxy-N-methyl-propanamide

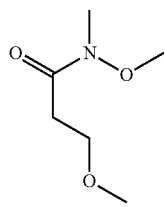

A solution of 3-methoxypropanoic acid (62 g, 577.7 mmol) in DCM (1200 mL) is treated portion-wise slowly with 1,1'-carbonyldiimidazole (103 g, 635.2 mmol) and stirred at room temperature for 2 hours. N,O-dimethylhydroxylamine hydrochloride (62 g, 635.6 mmol) is added and the mixture is stirred at room temperature overnight. The mixture is washed with water (2×), 0.1M aq HCl (2×), and with saturated aqueous sodium bicarbonate (2×), dried over magnesium sulfate, filtered and concentrated to dryness to give the crude material. The crude material is chromatographed over silica gel eluting with a gradient of 20-40% acetone in hexanes. The resulting oil is dried overnight under vacuum to give the title compound (69.5 g, 81.7%). $^1$H NMR (CDCl$_3$) δ 2.72 (t, 2H), 3.2 (s, 3H), 3.38 (s, 3H), 3.7 (m, 5H).

PREPARATION 21

2,2,2-Trifluoro-N-[(1S)-1-[4-(1-hydroxy-3-methoxy-propyl)phenyl]ethyl]acetamide

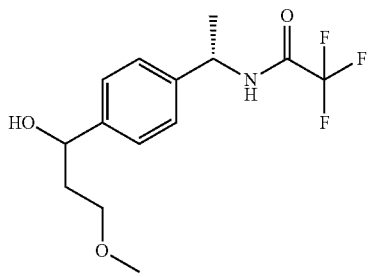 [SMILES: COCCC(O)c1ccc([C@H](C)NC(=O)C(F)(F)F)cc1]

2,2,2-Trifluoro-N-[(1S)-1-[4-(3-methoxypropanoyl)phenyl]ethyl]acetamide (23.62 g, 73.98 mmol, 95 mass %) is dissolved in MeOH (700 mL) and treated with sodium borohydride (5.6 g, 150 mmol). After stirring at room temperature for 2 hours the mixture is treated with saturated aqueous ammonium chloride and the MeOH is evaporated. The resulting material is partitioned between water and EtOAc, separated and the combined organics are dried over Na$_2$SO$_4$, filtered, and concentrated to dryness. The crude material is chromatographed on silica gel eluting with 40% EtOAc in hexanes to give the title compound as a white solid (17.82 g, 79%). MS (m/z): 306 (M+H).

PREPARATION 22 tert-Butyl 4-[3-methoxy-1-[4-[(1S)-1-[(2,2,2-trifluoroacetyl)amino]ethyl]phenyl]propyl]piperazine-1-carboxylate

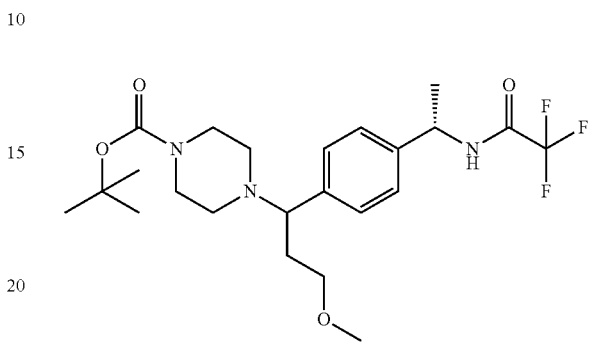

2,2,2-trifluoro-N-[(1S)-1-[4-(1-hydroxy-3-methoxy-propyl)phenyl]ethyl]acetamide (21.76 g, 71.27 mmol) is dissolved in DCM (350 mL) and cooled to −10° C. Thionyl chloride (26.12 g, 16 mL, 219.6 mmol) is added dropwise and the reaction is stirred for 2 hours. The mixture is concentrated to dryness, re-dissolved in DCM, and re-concentrated. The crude material is dissolved in ACN (300 mL) and t-butyl piperazine-1-carboxylate (26.55 g, 142.6 mmol), potassium carbonate (39.5 g, 286 mmol) and potassium iodide (12.0 g, 72.3 mmol) are added. The mixture is heated to 80° C. for 72 hours. The resulting white solid is filtered and washed with EtOAc. The combined filtrates are washed with aqueous ammonium chloride, dried over magnesium sulfate, filtered, and concentrated. The crude material is chromatographed on silica gel eluting with a gradient of 40-80% EtOAc in hexanes to give the title compound as a white foam (29.63 g, 88%). MS (m/z): 474 (M+H).

PREPARATION 23 tert-Butyl 4-[1-[4-(1S)-1-aminoethyl]phenyl]-3-methoxy-propyl]piperazine-1-carboxylate, diastereomer 1

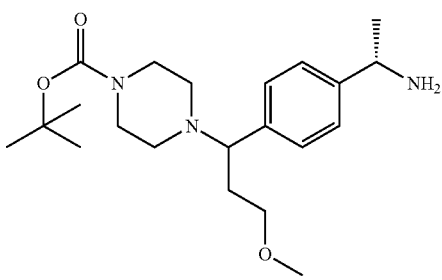 [SMILES: COCCC(c1ccc([C@H](C)N)cc1)N1CCN(C(=O)OC(C)(C)C)CC1]

PREPARATION 24 tert-Butyl 4-[1-[4-(1S)-1-aminoethyl]phenyl]-3-methoxy-propyl]piperazine-1-carboxylate, diastereomer 2

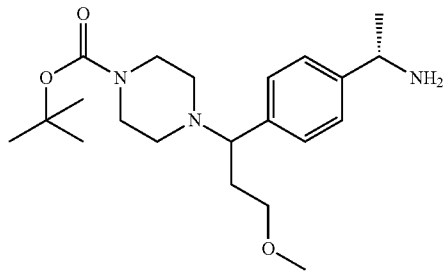 [SMILES: COCCC(c1ccc([C@H](C)N)cc1)N1CCN(C(=O)OC(C)(C)C)CC1]

To a solution of tert-butyl 4-[3-methoxy-1-[4-[(1S)-1-[(2,2,2-trifluoroacetyl)amino]-ethyl]propyl]piperazine-1-carboxylate (29.60 g, 62.5 mmol) in EtOH (310 mL) is added aq potassium hydroxide (63 mL, 5 M). The solution is stirred for 4 hours at room temperature and then the mixture is concentrated to dryness. The crude residue is treated with water and saturated aqueous sodium bicarbonate and extracted with DCM (3×). The combined organic extracts are dried over sodium sulfate, filtered, and concentrated to give the title compound (23.6 g) which is dissolved in MeOH (236 mL) and separated into individual diastereomers by chiral SFC chromatography using the following conditions: column: Lux Cellulose-1, (5×25 cm); injection volume: 1 mL every 2.5 minutes, eluent 15% MeOH/CO₂, detection wavelength 230 nm; flow rate 300 g/min; column temperature: 40° C.; BPR Setpoint: 100 bar; BPR temperature: 40° C. The title compound of Preparation 28 is obtained from the first eluting peak as a clear viscous yellow oil (10.1 g, 42.8%, 96.6% de). MS (m/z): 378 (M+H). The compound of Preparation 29 is isolated as the second eluting peak as a clear viscous yellow oil (10.3 g, 43.6%, 95.2% de). MS (m/z): 378 (M+H).

PREPARATION 25

7-[[(1S)-1-[4-(1-Chloro-2-cyclopropyl-ethyl)phenyl]ethyl]amino]-1-ethyl-4H-pyrimido[4,5-d][1,3]oxazin-2-one

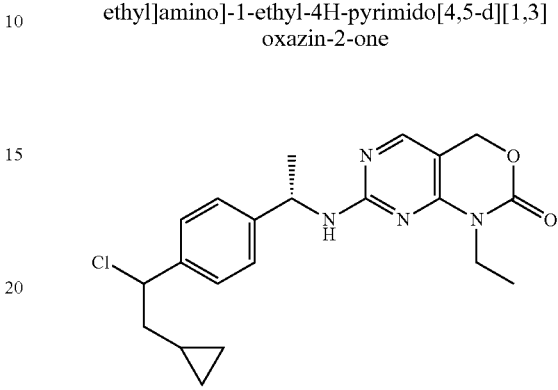

Thionyl chloride (0.23 mL, 3.219 mmol) is added to a mixture of 7-[[(1S)-1-[4-(2-cyclopropyl-1-hydroxy-ethyl)phenyl]ethyl]amino]-1-ethyl-4H-pyrimido[4,5-d][1,3]oxazin-2-one (432 mg, 1.03 mmol) and potassium carbonate (741 mg, 5.37 mmol) in DCM (20 mL) and the mixture is stirred at room temperature for 20 minutes. The mixture is filtered through diatomaceous earth and concentrated to give the title compound (518 mg, 1.07 mmol, 100%) as a white foam, which is used without further purification. ES/MS (m/z): 401.2/403.2 (M+H).

The following compounds are prepared essentially by the method of Preparation 25.

TABLE 5

| Prep. No. | Chemical name | Structure | ES/MS (m/z) (M + H) |
|---|---|---|---|
| 26 | N-[(1S)-1-[4-(1-Chloro-2-cyclopropyl-ethyl)phenyl]ethyl]-2,2,2-trifluoro-acetamide | 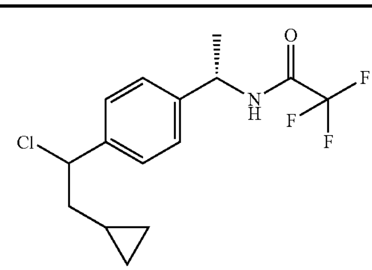 | 318 |
| 27 | N-[(1S)-1-[4-(1-Chloro-3-methyl-butyl)phenylethyl]-2,2,2-trifluoro-acetamide | 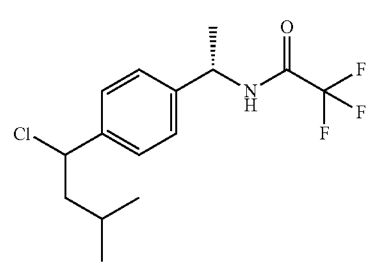 [SMILES: CC(C)CC(Cl)c1ccc([C@H](C)NC(=O)C(F)(F)F)cc1] | 320 |

TABLE 5-continued

| Prep. No. | Chemical name | Structure | ES/MS (m/z) (M + H) |
|---|---|---|---|
| 28 | N-[(1S)-1-[4-(1-Chloropropyl)phenyl]ethyl]-2,2,2-trifluoro-acetamide | 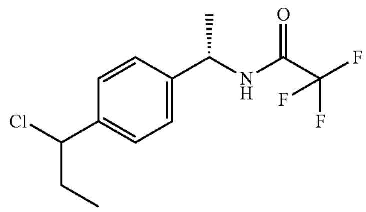 [SMILES: CCC(Cl)c1ccc([C@H](C)NC(=O)C(F)(F)F)cc1] | 311 (M + NH₄) |

PREPARATION 29 tert-Butyl 4-[(1R)-2-cyclopropyl-1-[4-[(1S)-1-[(1-ethyl-2-oxo-4H-pyrimido[4,5-d][1,3]oxazin-7-yl)amino]ethyl]phenyl]ethyl]piperazine-1-carboxylate

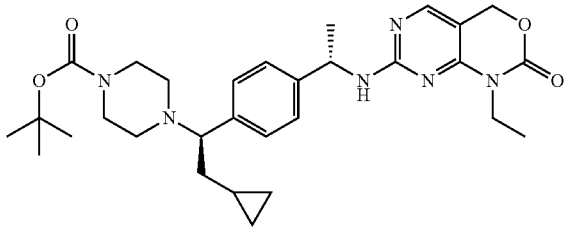 [SMILES: CCN1C(=O)OCc2cnc(N[C@@H](C)c3ccc([C@@H](CC4CC4)N4CCN(C(=O)OC(C)(C)C)CC4)cc3)nc21]

To a solution of tert-butyl 4-[(1R)-1-[4-[(1S)-1-aminoethyl]phenyl]-2-cyclopropyl-ethyl]piperazine-1-carboxylate (864 mg, 3.35 mmol), and 1-ethyl-7-(methylsulfonyl)-1,4-dihydro-2H-pyrimido[4,5-d][1,3]oxazin-2-one (1.14 g, 3.05 mmol), in DMSO (15 mL) is added CsF (1.39 g, 9.15 mmol) and DIPEA (0.80 mL, 4.6 mmol). The mixture is stirred at 60° C. for 1.5 hours. The mixture is cooled to room temperature, diluted with EtOAc, and washed with water (2×). The combined aqueous washes are extracted with EtOAc and the combined organic extracts are dried (Na₂SO₄), filtered, and concentrated to dryness. The resulting crude product is purified by silica gel chromatography eluting with a gradient of 55% to 95% EtOAc in hexanes to give the title compound as a colorless solid (1.47 g, 88%). MS (m/z): 551.3 (M+H).

The following compounds are prepared essentially by the method of Preparation 29.

TABLE 6

| Prep. No. | Chemical name | Structure | ES/MS (m/z) (M + H) |
|---|---|---|---|
| 30 | tert-Butyl 4-[(1S)-2-cyclopropyl-1-[4-[(1S)-1-[(1-ethyl-2-oxo-4H-pyrimido[4,5-d][1,3]oxazin-7-yl)amino]ethyl]phenyl]ethyl]piperazine-1-carboxylate, | 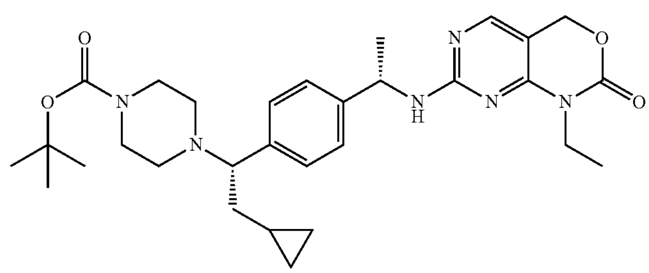 [SMILES: CCN1C(=O)OCc2cnc(N[C@@H](C)c3ccc([C@H](CC4CC4)N4CCN(C(=O)OC(C)(C)C)CC4)cc3)nc21] | 551 |
| 31 | tert-Butyl 4-[1-[4-[(1S)-1-[(1-ethyl-2-oxo-4H-pyrimido[4,5-d][1,3]oxazin-7-yl)amino]ethyl]phenyl]-3-methoxy-propyl]piperazine-1-carboxylate (diastereomer 1) | 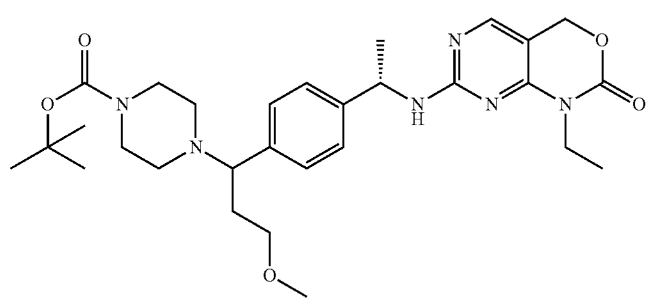 [SMILES: CCN1C(=O)OCc2cnc(N[C@@H](C)c3ccc(C(CCOC)N4CCN(C(=O)OC(C)(C)C)CC4)cc3)nc21] | 555 |

TABLE 6-continued

| Prep. No. | Chemical name | Structure | ES/MS (m/z) (M + H) |
|---|---|---|---|
| 32 | tert-Butyl 4-[1-[4-[(1S)-1-[(1-ethyl-2-oxo-4H-pyrimido[4,5-d][1,3]oxazin-7-yl)amino]ethyl]phenyl]-3-methoxy-propyl]piperazine-1-carboxylate (diastereomer 2) | 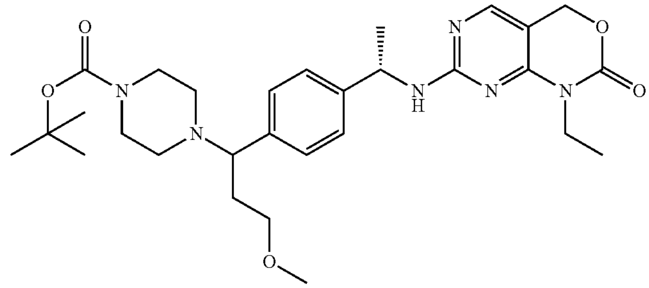 [SMILES: CCN1C(=O)OCc2cnc(N[C@@H](C)c3ccc(C(CCOC)N4CCN(C(=O)OC(C)(C)C)CC4)cc3)nc21] | 555 |
| 33 | tert-Butyl 4-[2-cyclopropyl-1-[4-[(1S)-1-[(1-methyl-2-oxo-4H-pyrimido[4,5-d][1,3]oxazin-7-yl)amino]ethyl]phenyl]ethyl]piperazine-1-carboxylate (diastereomer 1) | 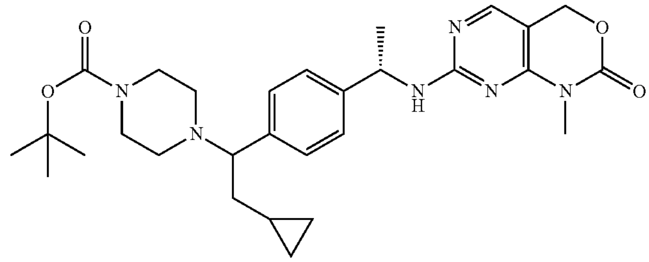 [SMILES: C[C@H](Nc1ncc2c(n1)N(C)C(=O)OC2)c1ccc(C(CC2CC2)N2CCN(C(=O)OC(C)(C)C)CC2)cc1] | 537 |
| 34 | tert-Butyl 4-[2-cyclopropyl-1-[4-[(1S)-1-[(1-methyl-2-oxo-4H-pyrimido[4,5-d][1,3]oxazin-7-yl)amino]ethyl]phenyl]ethyl]piperazine-1-carboxylate (diastereomer 2) | 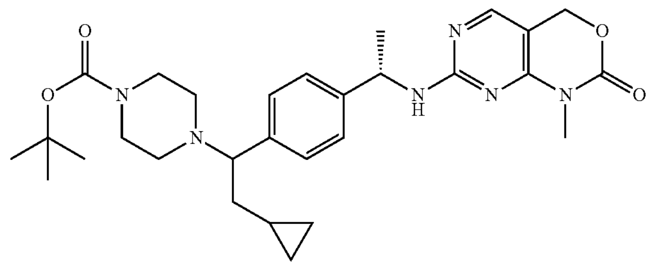 [SMILES: C[C@H](Nc1ncc2c(n1)N(C)C(=O)OC2)c1ccc(C(CC2CC2)N2CCN(C(=O)OC(C)(C)C)CC2)cc1] | 537 |
| 35 | tert-Butyl 4-[1-[4-[(1S)-1-[(1-ethyl-2-oxo-4H-pyrimido[4,5-d][1,3]oxazin-7-yl)amino]ethyl]phenyl]-3-methyl-butyl]piperazine-1-carboxylate | 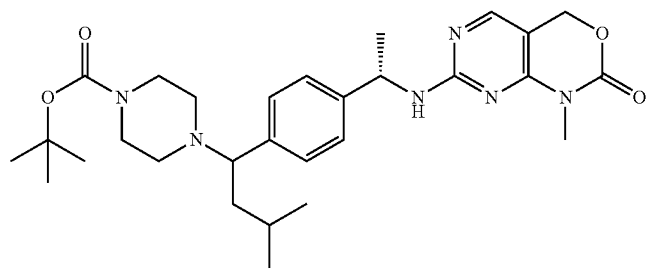 [SMILES: CC(C)CC(c1ccc([C@H](C)Nc2ncc3c(n2)N(C)C(=O)OC3)cc1)N1CCN(C(=O)OC(C)(C)C)CC1] | 553 |
| 36 | tert-Butyl 4-[(1R/S)-1-[4-[(1S)-1-[(1-ethyl-2-oxo-4H-pyrimido[4,5-d][1,3]oxazin-7-yl)amino]ethyl]phenyl]propyl]piperazine-1-carboxylate, isomer 1 | 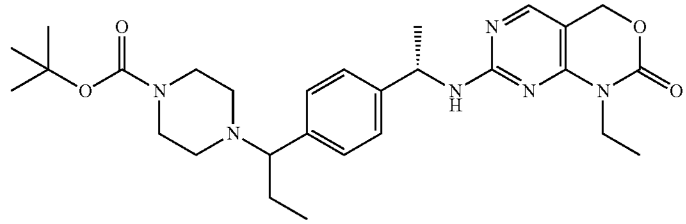 [SMILES: CCC(c1ccc([C@H](C)Nc2ncc3c(n2)N(CC)C(=O)OC3)cc1)N1CCN(C(=O)OC(C)(C)C)CC1] | 525 |

TABLE 6-continued

| Prep. No. | Chemical name | Structure | ES/MS (m/z) (M + H) |
|---|---|---|---|
| 37 | tert-Butyl 4-[(1R/S)-1-[4-[(1S)-1-[(1-ethyl-2-oxo-4H-pyrimido[4,5-d][1,3]oxazin-7-yl)amino]ethyl]phenyl]propyl]piperazine-1-carboxylate, isomer 2 | 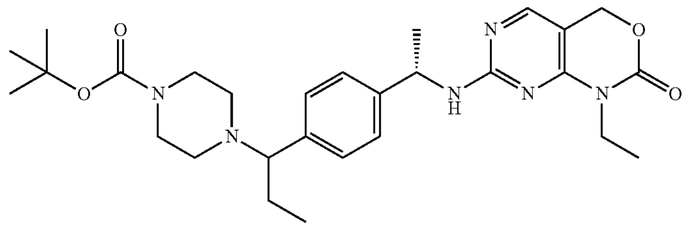 [SMILES: CCC(c1ccc([C@H](C)Nc2ncc3c(n2)N(CC)C(=O)OC3)cc1)N1CCN(C(=O)OC(C)(C)C)CC1] | 525 |
| 38 | 7-[[(1S)-1-[4-(2-Cyclopropyl-1-hydroxy-ethyl)phenyl]ethyl]amino]-1-ethyl-4H-pyrimido[4,5-d][1,3]oxazin-2-one | 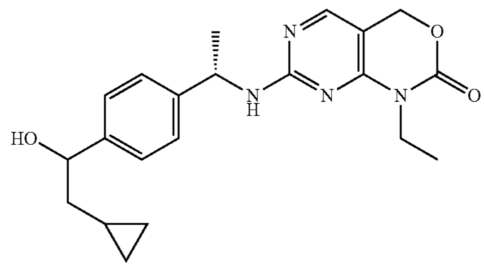 [SMILES: CCN1C(=O)OCc2cnc(N[C@@H](C)c3ccc(C(O)CC4CC4)cc3)nc21] | 383 |

PREPARATION 39

7-[[(1S)-1-[4-[(1R)-2-Cyclopropyl-1-piperazin-1-yl-ethyl]phenyl]ethyl]amino]-1-ethyl-4H-pyrimido[4,5-d][1,3]oxazin-2-one

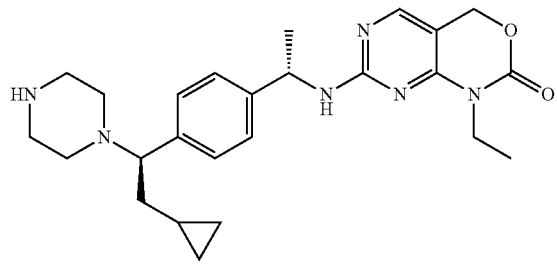

Hydrochloric acid (95 mL, 5.5 M in isopropanol, 520 mmol) is added dropwise to a solution of tert-butyl 4-[(1R)-2-cyclopropyl-1-[4-[(5S)-1-[(1-ethyl-2-oxo-4H-pyrimido[4,5-d][1,3]oxazin-7-yl)amino]ethyl]phenyl]ethyl]piperazine-1-carboxylate (29.45 g, 53.48 mmol) in EtOAc (570 mL) at 40° C. The mixture is allowed to stir 3 hours, at room temperature, and then water (300 mL) is added. The layers are separated and the organic layer is extracted with water (2×150 mL). The pH of the combined aqueous extracts are adjusted to pH 10 by the addition of 5 N NaOH resulting in the formation of a colorless solid. The solid is collected by filtration, washed with water, and air-dried to give the title compound (25.18 g, 99%) as a colorless solid. MS (m/z): 451.2 ( M+H).

The following compound is prepared essentially by the method of Preparation 39.

TABLE 7

| Prep. No. | Chemical name | Structure | ES/MS (m/z) (M + H) |
|---|---|---|---|
| 40 | 7-[[(1S)-1-[4-[(1S)-2-Cyclopropyl-1-piperazin-1-yl-ethyl]phenyl]ethyl]amino]-1-ethyl-4H-pyrimido[4,5-d][1,3]oxazin-2-one | 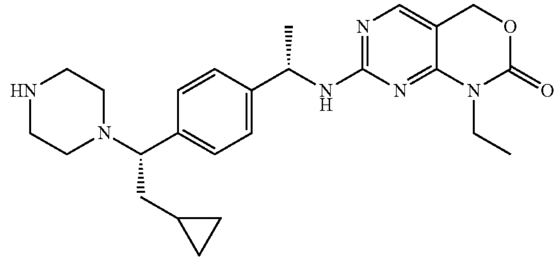 [SMILES: CCN1C(=O)OCc2cnc(N[C@@H](C)c3ccc([C@H](CC4CC4)N4CCNCC4)cc3)nc21] | 451 |

PREPARATION 41

7-[[(1S)-1-[4-(2-Cyclopropyl-1-piperazin-1-yl-ethyl)phenyl]ethyl]amino]-1-methyl-4H-pyrimido[4,5-d][1,3]oxazin-2-one, diastereomer 1

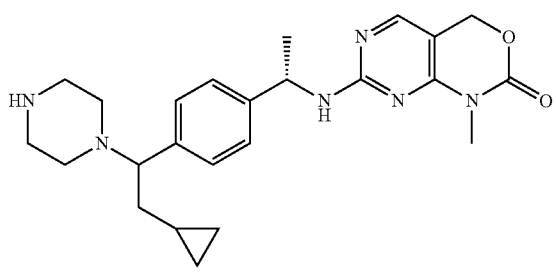 [SMILES: C[C@H](Nc1ncc2c(n1)N(C)C(=O)OC2)c1ccc(C(CC2CC2)N2CCNCC2)cc1]

tert-Butyl 4-[2-cyclopropyl-1-[4-[(1S)-1-[(1-methyl-2-oxo-4H-pyrimido[4,5-d][1,3]oxazin-7-yl)amino]ethyl]phenyl]ethyl]piperazine-1-carboxylate, diastereomer 1 (245 mg, 0.46 mmol) is dissolved in DCM (2.5 mL). TFA (0.7 mL, 9 mmol) is added and the reaction is stirred at room temperature for 90 minutes. The mixture is quenched with 20% aq $K_2CO_3$ and extracted with DCM (3×). The combined organic extracts are dried over $Na_2SO_4$, filtered, and concentrated to dryness on high vacuum overnight to give the title compound as a white foam, (196 mg, 88.5%). MS (m/z): 437 (M+H).

The following compounds are prepared essentially by the method of Preparation 41.

TABLE 8

| Prep. No. | Chemical name | Structure | ES/MS (m/z) (M + H) |
|---|---|---|---|
| 42 | 7-[[(1S)-1-[4-(2-Cyclopropyl-1-piperazin-1-yl-ethyl)phenyl]ethyl]amino]-1-methyl-4H-pyrimido[4,5-d][1,3]oxazin-2-one, diastereomer 2 | 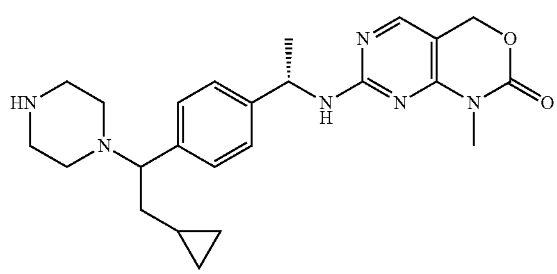 [SMILES: C[C@H](Nc1ncc2c(n1)N(C)C(=O)OC2)c1ccc(C(CC2CC2)N2CCNCC2)cc1] | 437 |
| 43 | 1-Ethyl-7-[[(1S)-1-[4-(3-methyl-1-piperazin-1-yl-butyl)phenyl]ethyl]amino]-4H-pyrimido[4,5-d][1,3]oxazin-2-one, isomer 1 | 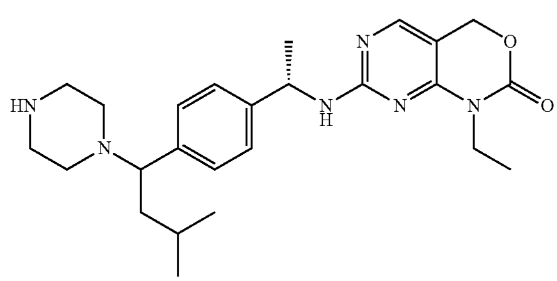 [SMILES: CCN1C(=O)OCc2cnc(N[C@@H](C)c3ccc(C(CC(C)C)N4CCNCC4)cc3)nc21] | 453 |
| 44 | 1-Ethyl-7-[[(1S)-1-[4-(3-methyl-1-piperazin-1-yl-butyl)phenyl]ethyl]amino]-4H-pyrimido[4,5-d][1,3]oxazin-2-one, isomer 2 | 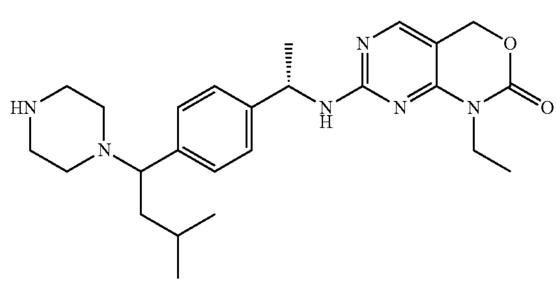 [SMILES: CCN1C(=O)OCc2cnc(N[C@@H](C)c3ccc(C(CC(C)C)N4CCNCC4)cc3)nc21] | 453 |

TABLE 8-continued

| Prep. No. | Chemical name | Structure | ES/MS (m/z) (M + H) |
|---|---|---|---|
| 45 | 7-[[(1S)-1-[4-(2-Cyclopropyl-1-piperazin-1-yl-ethyl)phenyl]ethyl]amino]-1-methyl-4H-pyrido[4,3-d][1,3]oxazin-2-one, isomer 1 | 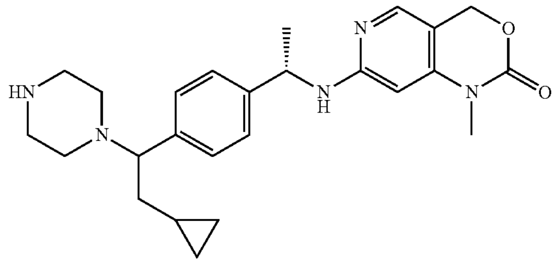 [SMILES: C[C@H](Nc1cc2c(cn1)COC(=O)N2C)c1ccc(C(CC2CC2)N2CCNCC2)cc1] | 436 |
| 46 | 7-[[(1S)-1-[4-(2-Cyclopropyl-1-piperazin-1-yl-ethyl)phenyl]ethyl]amino]-1-methyl-4H-pyrido[4,3-d][1,3]oxazin-2-one, isomer 2 | 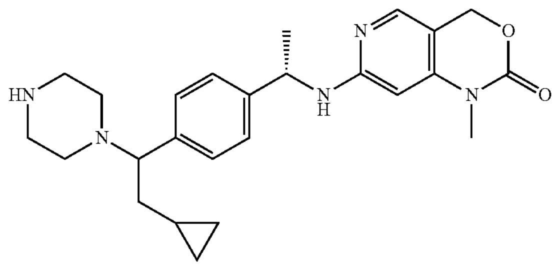 [SMILES: C[C@H](Nc1cc2c(cn1)COC(=O)N2C)c1ccc(C(CC2CC2)N2CCNCC2)cc1] | 436 |
| 47 | 1-Ethyl-7-[[(1S)-1-[4-[(1R/S)-1-piperazin-1-ylpropyl]phenyl]ethyl]amino]-4H-pyrimido[4,5-d][1,3]oxazin-2-one, isomer 1 | 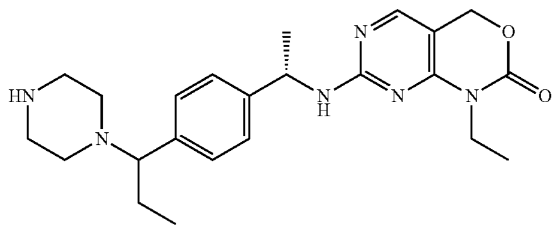 [SMILES: CCC(c1ccc([C@H](C)Nc2ncc3c(n2)N(CC)C(=O)OC3)cc1)N1CCNCC1] | 425 |
| 48 | 1-Ethyl-7-[[(1S)-1-[4-[(1R/S)-1-piperazin-1-ylpropyl]phenyl]ethyl]amino]-4H-pyrimido[4,5-d][1,3]oxazin-2-one, isomer2 | 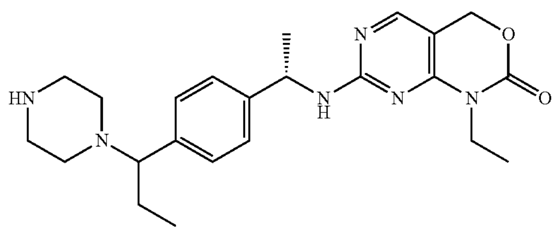 [SMILES: CCC(c1ccc([C@H](C)Nc2ncc3c(n2)N(CC)C(=O)OC3)cc1)N1CCNCC1] | 425 |

PREPARATION 49

7-[[(1S)-1-[4-(2-Cyclopropyl-1-piperazin-1-yl-ethyl)phenyl]ethyl]amino]-1-ethyl-4H-pyrimido[4,5-d][1,3]oxazin-2-one

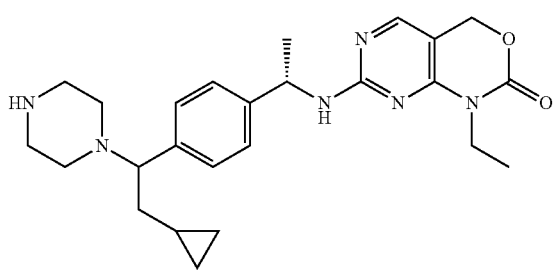 [SMILES: CCN1C(=O)OCc2cnc(N[C@@H](C)c3ccc(C(CC4CC4)N4CCNCC4)cc3)nc21]

A mixture of 7-[[(1S)-1-[4-(1-chloro-2-cyclopropyl-ethyl)phenyl]ethyl]amino]-1-ethyl-4H-pyrimido[4,5-d][1,3]oxazin-2-one (518 mg, 1.07 mmol), potassium carbonate (445 mg, 3.217 mmol), sodium iodide (161 mg, 1.07 mmol) and piperazine (277 mg, 3.22 mmol) in ACN (3 mL) is heated in a sealed vial to 70° C. After ~8 hours, the mixture is cooled to room temperature, diluted with EtOAc, filtered through diatomaceous earth, and concentrated. The crude material is purified on silica gel eluting with a gradient of 1% to 7% 3 M $NH_3$/MeOH in DCM to give the title compound (306 mg, 0.66 mmol, 62%) as a white solid. ES/MS (m/z): 451.2 (M+H).

The following compounds are prepared essentially by the method of Preparation 49 using the appropriate protected piperazine.

TABLE 9

| Prep. No. | Chemical name | Structure | ES/MS (m/z) (M + H) |
|---|---|---|---|
| 50 | tert-Butyl 4-[2-cyclopropyl-1-[4-[(1S)-1-[(2,2,2-trifluoroacetyl)amino]ethyl]phenyl]ethyl]piperazine-1-carboxylate | 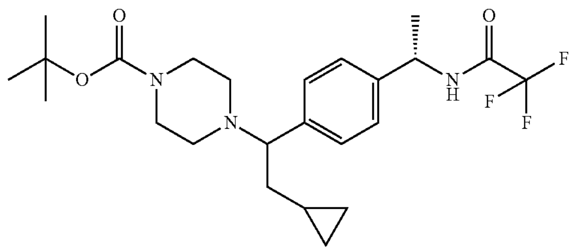 [SMILES: C[C@H](NC(=O)C(F)(F)F)c1ccc(C(CC2CC2)N2CCN(C(=O)OC(C)(C)C)CC2)cc1] | 470 |
| 51 | tert-Butyl 4-[3-methyl-1-[4-[(1S)-1-[(2,2,2-trifluoroacetyl)amino]ethyl]phenyl]butyl]piperazine-1-carboxylate | 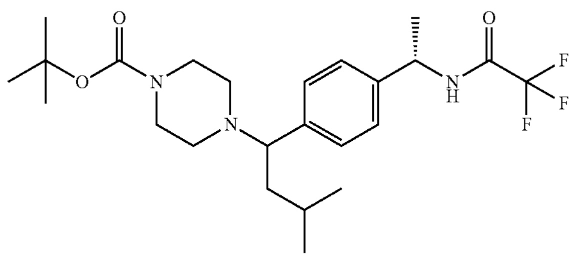 [SMILES: CC(C)CC(c1ccc([C@H](C)NC(=O)C(F)(F)F)cc1)N1CCN(C(=O)OC(C)(C)C)CC1] | 472 |
| 52 | tert-Butyl 4-[1-[4-[(1S)-1-[(2,2,2-trifluoroacetyl)amino]ethyl]phenyl]propyl]piperazine-1-carboxylate | 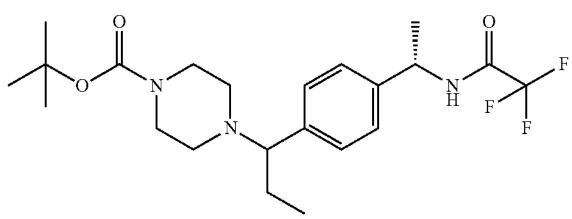 [SMILES: CCC(c1ccc([C@H](C)NC(=O)C(F)(F)F)cc1)N1CCN(C(=O)OC(C)(C)C)CC1] | 444 |

PREPARATION 53 tert-Butyl 4-[1-[4-[(1S)-1-[(2,2,2-trifluoroacetyl)amino]ethyl]phenyl]propyl]piperazine-1-carboxylate, isomer 1

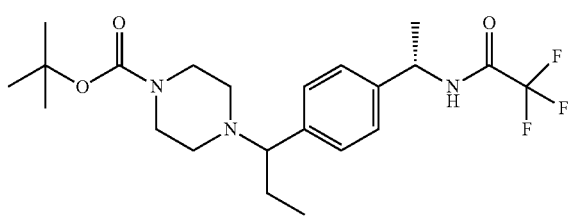 [SMILES: CCC(c1ccc([C@H](C)NC(=O)C(F)(F)F)cc1)N1CCN(C(=O)OC(C)(C)C)CC1]

PREPARATION 54 tert-Butyl 4-[1-[4-[(1S)-1-[(2,2,2-trifluoroacetyl)amino]ethyl]phenyl]propyl]piperazine-1-carboxylate, isomer 2

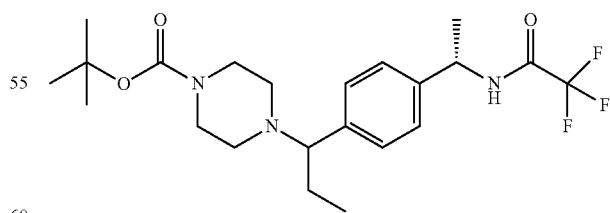

tert-Butyl 4-[1-[4-[(1S)-1-[(2,2,2-trifluoroacetyl)amino]ethyl]phenyl]propyl]piperazine-1-carboxylate (29.2 g, 65.8 mmol) is dissolved in MeOH (584 mL) and resolved by chiral SFC chromatography using the following conditions: column: Chiralpak AD-H, 5×25 cm; eluent 85/15 CO$_2$/MeOH with 0.5% dimethylethylamine; flow rate 300 g/min;

detection wavelength 230 nm; column temperature 40° C.; BPR setpoint 100 bar; 40° C. solvent temperature. Isomer 1 is isolated as the first eluting peak (14.15 g, 31.9 mmol). ES/MS (m/z): 444 (M+H). Isomer 2 is isolated as the second eluting peak (13.87 g, 31.3 mmol). ES/MS (m/z): 444 (M+H).

PREPARATION 55 tert-Butyl 4-[1-[4-[(1S)-1-[(1-ethyl-2-oxo-4H-pyrimido[4,5-d][1,3]oxazin-7-yl)amino]ethyl]phenyl]-3-methyl-butyl]piperazine-1-carboxylate, isomer 1

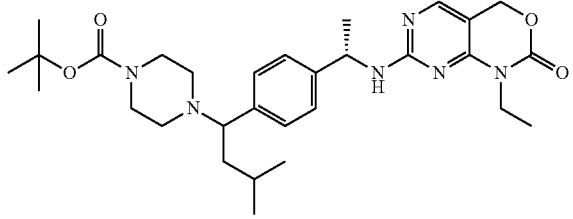 [SMILES: CCN1C(=O)OCc2cnc(N[C@@H](C)c3ccc(C(CC(C)C)N4CCN(C(=O)OC(C)(C)C)CC4)cc3)nc21]

PREPARATION 56 tert-Butyl 4-[1-[4-[(1S)-1-[(1-ethyl-2-oxo-4H-pyrimido[4,5-d][1,3]oxazin-7-yl)amino]ethyl]phenyl]-3-methyl-butyl]piperazine-1-carboxylate, isomer 2

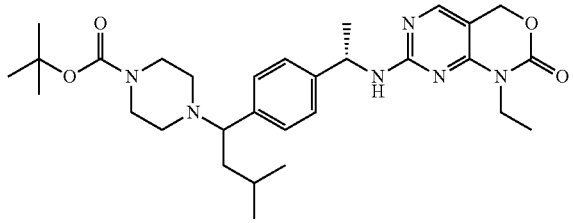 [SMILES: CCN1C(=O)OCc2cnc(N[C@@H](C)c3ccc(C(CC(C)C)N4CCN(C(=O)OC(C)(C)C)CC4)cc3)nc21]

tert-Butyl 4-[1-[4-[(1S)-1-[(1-ethyl-2-oxo-4H-pyrimido[4,5-d][1,3]oxazin-7-yl)amino]ethyl]phenyl]-3-methyl-butyl]piperazine-1-carboxylate (2.6 g, 4.70 mmol) is dissolved in 4:1 isopropanol:chloroform (50 mL) and resolved by chiral SFC chromatography using the following conditions: column: Chiralpak AD-H, 5×25 cm; injection volume 1 mL; eluent 75/25 $CO_2$/IPA with 0.5% dimethylethylamine; flow rate 280 g/min; detection wavelength 240 nm; column temperature 40° C.; BPR setpoint 100 bar; 40° C. solvent temperature. Preparation 45 is isolated as the first eluting peak (1.02 g, 1.89 mmol). ES/MS (m/z): 553.4 (M+H). Preparation 46 is isolated as the second eluting peak (1.05 g, 1.90 mmol). ES/MS (m/z): 553.4 (M+H).

EXAMPLE 1

7-[[(1S)-1-[4-[(1R)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one

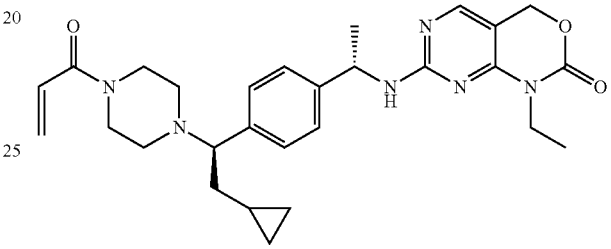

Acryloyl chloride (305 3.75 mmol, in 2 mL DCM) is added dropwise to a solution of 7-[[(1S)-1-[4-[(1R)-2-cyclopropyl-1-piperazin-1-yl-ethyl]phenyl]ethyl]amino]-1-ethyl-4H-pyrimido[4,5-d][1,3]oxazin-2-one (1.73 g, 3.26 mmol) in DCM at −78° C. After 2 minutes at −78° C. a few drops of MeOH are added followed by saturated aqueous sodium bicarbonate and the mixture is allowed to warm to room temperature. DCM is added, the layers are separated, and the aqueous layer is extracted with DCM. The combined organic extracts are dried ($Na_2SO_4$), filtered, and concentrated to dryness. The resulting crude product is purified by silica gel chromatography (25% to 40% Solvent A in Solvent B where Solvent A is 10% MeOH/acetone and Solvent B is hexanes) to give the title compound as a colorless solid (1.16 g, 70%). MS (m/z): 505.3 (M+H).

The following compounds are prepared essentially by the method of Example 1.

TABLE 11

| Ex. No. | Chemical name | Structure | ES/MS (m/z) (M + H) |
|---|---|---|---|
| 2 | 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one | 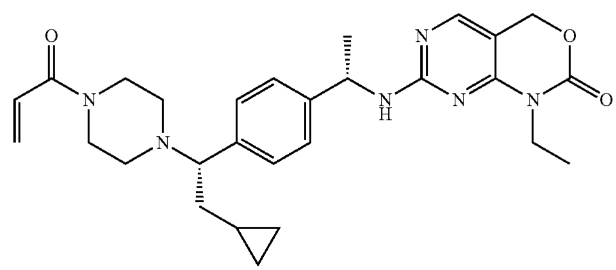 [SMILES: C=CC(=O)N1CCN([C@@H](CC2CC2)c2ccc([C@H](C)Nc3ncc4c(n3)N(CC)C(=O)OC4)cc2)CC1] | 505 |

TABLE 11-continued

| Ex. No. | Chemical name | Structure | ES/MS (m/z) (M + H) |
|---|---|---|---|
| 3 | 7-[[(1S)-1-[4-[2-Cyclopropyl-1-(4-prop-2-enoylpiperazin-1-yl)ethyl]phenyl]ethyl]amino]-1-methyl-4H-pyrimido[4,5-d][1,3]oxazin-2-one, diastereomer 1 | 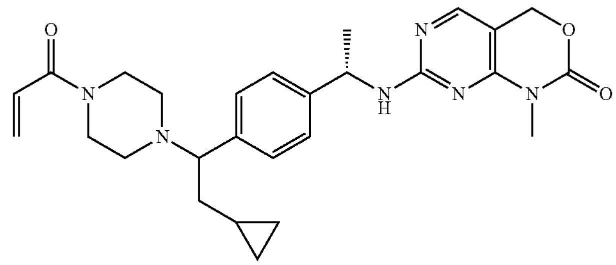 [SMILES: C=CC(=O)N1CCN(C(CC2CC2)c2ccc([C@H](C)Nc3ncc4c(n3)N(C)C(=O)OC4)cc2)CC1] | 491 |
| 4 | 7-[[(1S)-1-[4-[2-Cyclopropyl-1-(4-prop-2-enoylpiperazin-1-yl)ethyl]phenyl]ethyl]amino]-1-methyl-4H-pyrimido[4,5-d][1,3]oxazin-2-one, diastereomer 2 | 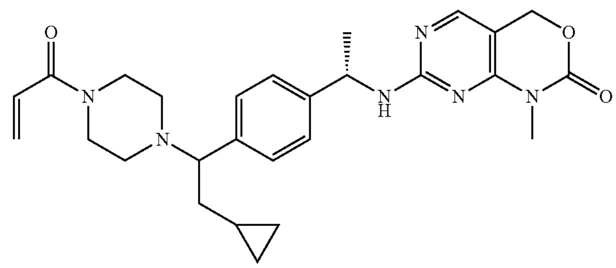 [SMILES: C=CC(=O)N1CCN(C(CC2CC2)c2ccc([C@H](C)Nc3ncc4c(n3)N(C)C(=O)OC4)cc2)CC1] | 491 |
| 5 | 7-[[(1S)-1-[4-[2-Cyclopropyl-1-(4-prop-2-enoylpiperazin-1-yl)ethyl]phenyl]ethyl]amino]-1-ethyl-4H-pyrimido[4,5-d][1,3]oxazin-2-one | 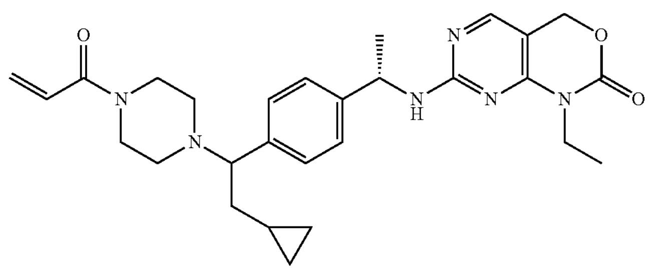 [SMILES: C=CC(=O)N1CCN(C(CC2CC2)c2ccc([C@H](C)Nc3ncc4c(n3)N(CC)C(=O)OC4)cc2)CC1] | 505 |
| 6 | 1-Ethyl-7-[[(1S)-1-[4-[3-methyl-1-(4-prop-2-enoylpiperazin-1-yl)butyl]phenyl]ethyl]amino]-4H-pyrimido[4,5-d][1,3]oxazin-2-one | 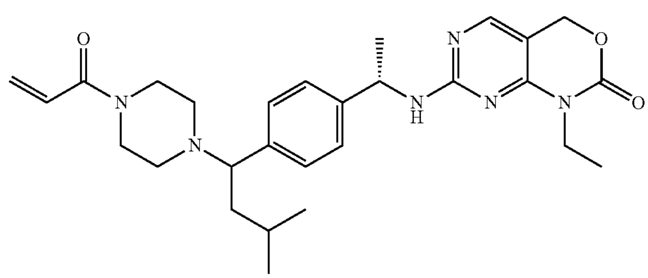 [SMILES: C=CC(=O)N1CCN(C(CC(C)C)c2ccc([C@H](C)Nc3ncc4c(n3)N(CC)C(=O)OC4)cc2)CC1] | 507 |
| 7 | 1-Ethyl-7-[[(1S)-1-[4-[3-methyl-1-(4-prop-2-enoylpiperazin-1-yl)butyl]phenyl]ethyl]amino]-4H-pyrimido[4,5-d][1,3]oxazin-2-one, isomer 1 | 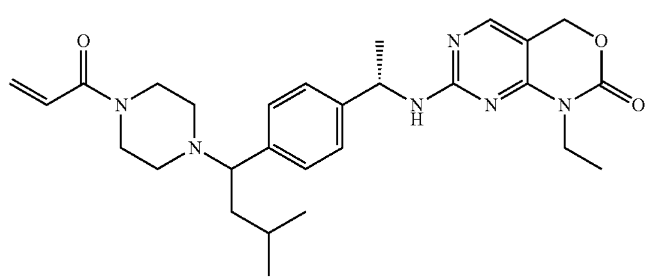 [SMILES: C=CC(=O)N1CCN(C(CC(C)C)c2ccc([C@H](C)Nc3ncc4c(n3)N(CC)C(=O)OC4)cc2)CC1] | 507 |

TABLE 11-continued

| Ex. No. | Chemical name | Structure | ES/MS (m/z) (M + H) |
|---|---|---|---|
| 8 | 1-Ethyl-7-[[(1S)-1-[4-[3-methyl-1-(4-prop-2-enoylpiperazin-1-yl)butyl]phenyl]ethyl]amino]-4H-pyrimido[4,5-d][1,3]oxazin-2-one, isomer 2 | 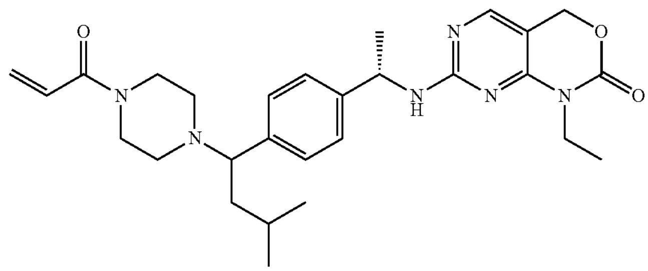 [SMILES: C=CC(=O)N1CCN(C(CC(C)C)c2ccc([C@H](C)Nc3ncc4c(n3)N(CC)C(=O)OC4)cc2)CC1] | 507 |
| 9 | 7-[[(1S)-1-[4-[2-Cyclopropyl-1-(4-prop-2-enoylpiperazin-1-yl)ethyl]phenyl]ethyl]amino]-1-methyl-4H-pyrido[4,3-d][1,3]oxazin-2-one, isomer 1 | 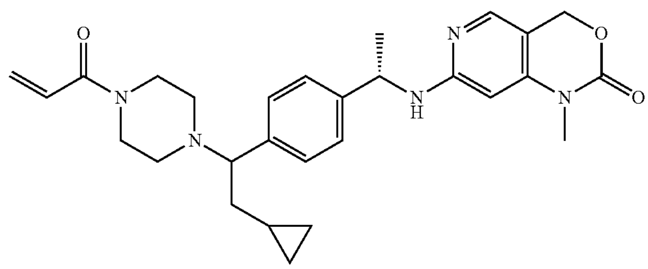 [SMILES: C=CC(=O)N1CCN(C(CC2CC2)c2ccc([C@H](C)Nc3cc4c(cn3)COC(=O)N4C)cc2)CC1] | 490 |
| 10 | 7-[[(1S)-1-[4-[2-Cyclopropyl-1-(4-prop-2-enoylpiperazin-1-yl)ethyl]phenyl]ethyl]amino]-1-methyl-4H-pyrido[4,3-d][1,3]oxazin-2-one, isomer 2 | 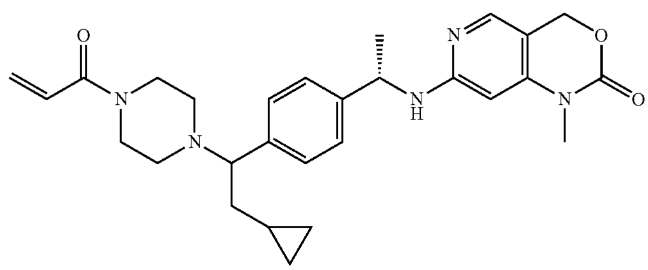 [SMILES: C=CC(=O)N1CCN(C(CC2CC2)c2ccc([C@H](C)Nc3cc4c(cn3)COC(=O)N4C)cc2)CC1] | 490 |
| 11 | 1-Ethyl-7-[[(1S)-1-[4-[(1R/S)-1-(4-prop-2-enoylpiperazin-1-yl)propyl]phenyl]ethyl]amino]-4H-pyrimido[4,5-d][1,3]oxazin-2-one, isomer 1 | 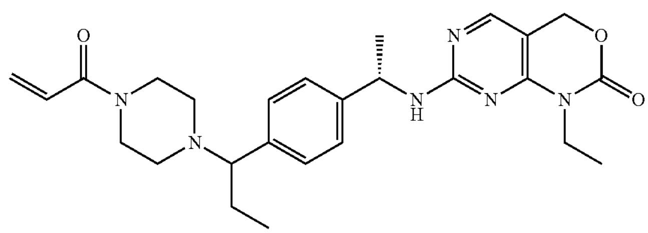 [SMILES: C=CC(=O)N1CCN(C(CC)c2ccc([C@H](C)Nc3ncc4c(n3)N(CC)C(=O)OC4)cc2)CC1] | 479 |
| 12 | 1-Ethyl-7-[[(1S)-1-[4-[(1R/S)-1-(4-prop-2-enoylpiperazin-1-yl)propyl]phenyl]ethyl]amino]-4H-pyrimido[4,5-d][1,3]oxazin-2-one, isomer 2 | 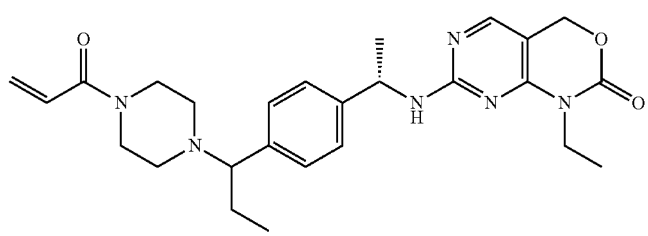 [SMILES: C=CC(=O)N1CCN(C(CC)c2ccc([C@H](C)Nc3ncc4c(n3)N(CC)C(=O)OC4)cc2)CC1] | 479 |

Determination of the IDH1 X-ray crystal structure in complex with 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3 ]oxazin-2-one.

The crystal structure of IDH1 in complex with 7-[[(1S)-1-[4-[(1S)-2-cyclopropyl-1-(4-prop-2-enoylpiperazin-1-yl) ethyl]phenyl]ethyl]amino]-1-ethyl-4H-pyrimido[4,5-d][1,3] oxazin-2-one is determined from X-ray diffraction data collected at the synchrotron beam-line APS 31-ID operated at the Advanced Photon Source at Argonne National Laboratory, Argonne, Ill. 60439. IDH1 protein with a R132H mutation is commercially available from multiple sources. Alternatively, IDH1 R132H protein may be isolated from a commercially available cell line harboring the mutation by techniques well known and routinely used by those skilled in the art. Crystals are obtained from sitting drop trays equilibrated at 21° C. with IDH1 protein with the mutation R132H at a concentration of 15 mg/ml in a buffer containing 10 mM HEPES pH 7.5, 150 mM sodium chloride, 10% glycerol, 5 mM dithiothreitol and 2 mM 7-[[(1S)-1-[4-[(1S)-

2-cyclopropyl-1-(4-prop-2-enoylpiperazin-1-yl)ethyl]phenyl]ethyl]amino]-1-ethyl-4H-pyrimido[4,5-d][1,3]oxazin-2-one, and mixed with an equal volume of reservoir solution containing 100 mM Bis Tris pH 5, 5% DMSO, 22% PEG 3350 and 200 mM Ammonium Sulfate. Crystals are soaked overnight in a solution containing 3 mM of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, before being transferred to a solution supplemented with 22% Ethylene Glycol and flash frozen for data collection. Diffraction data to 2.8 Å resolution is collected with X-ray radiation of wavelength 0.9793 Å. The crystals belong to Space Group $P4_32_12$ with cell parameters a=82.74 Å, b=82.74 Å, c=299.4 Å, $\alpha=\beta\gamma=90°$. The structure is determined by Molecular Replacement and contained one dimer molecule of IDH1. The difference electron density maps calculated after modelling the IDH1 protein have clear density for two bound molecules of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

The stereochemistry of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one is determined from the electron density, and both molecules of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one are modeled and the co-complex structure refined to R-factors of Rwork=0.192 and Rfree=0.228.

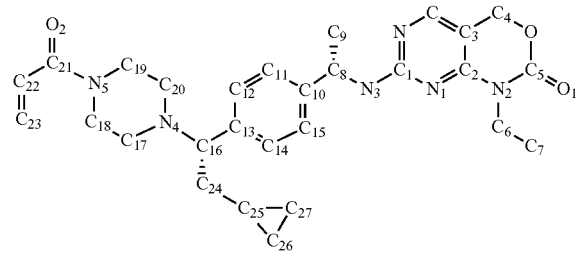

TABLE 12

Coordinates of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

| ATOM | X | Y | Z |
| --- | --- | --- | --- |
| O2 | 48.364 | 1.353 | −2.648 |
| C21 | 49.136 | 0.711 | −1.964 |
| C22 | 48.932 | −0.779 | −1.799 |
| C23 | 47.694 | −1.239 | −2.530 |
| N5 | 50.174 | 1.294 | −1.330 |
| C18 | 50.422 | 2.738 | −1.428 |
| C17 | 51.848 | 3.008 | −1.849 |
| C19 | 51.126 | 0.603 | −0.449 |
| C20 | 52.568 | 0.906 | −0.834 |
| N4 | 52.797 | 2.388 | −0.868 |
| C16 | 54.242 | 2.810 | −1.061 |
| C24 | 55.094 | 2.321 | 0.113 |
| C25 | 56.411 | 3.091 | 0.050 |
| C27 | 57.062 | 3.523 | 1.306 |
| C26 | 56.432 | 4.534 | 0.413 |
| C13 | 54.761 | 2.408 | −2.428 |
| C12 | 55.212 | 1.125 | −2.730 |
| C11 | 55.701 | 0.819 | −3.988 |
| C14 | 54.812 | 3.365 | −3.432 |

TABLE 12-continued

Coordinates of 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

| ATOM | X | Y | Z |
| --- | --- | --- | --- |
| C15 | 55.295 | 3.057 | −4.691 |
| C10 | 55.742 | 1.778 | −4.997 |
| C8 | 56.243 | 1.464 | −6.405 |
| C9 | 55.107 | 1.279 | −7.400 |
| N3 | 57.128 | 0.291 | −6.469 |
| C1 | 58.372 | 0.310 | −5.968 |
| N | 59.104 | −0.809 | −6.086 |
| N1 | 58.775 | 1.474 | −5.441 |
| C2 | 60.041 | 1.523 | −5.009 |
| N2 | 60.425 | 2.651 | −4.254 |
| C6 | 59.506 | 3.796 | −4.105 |
| C7 | 58.569 | 3.631 | −2.901 |
| C5 | 61.546 | 2.595 | −3.438 |
| O1 | 61.736 | 3.358 | −2.523 |
| O | 62.437 | 1.605 | −3.629 |
| C4 | 62.347 | 0.684 | −4.739 |
| C3 | 60.923 | 0.429 | −5.132 |
| C | 60.369 | −0.717 | −5.655 |

EXAMPLE 13

1-Ethyl-7-[[(1S)-1-[4-[3-methoxy-1-(4-prop-2-enoylpiperazin-1-yl)propyl]phenyl]ethyl]amino]-4H-pyrimido[4,5-d][1,3]oxazin-2-one, diastereomer 1

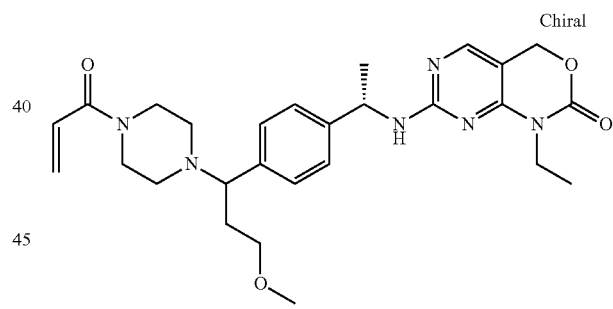

tert-Butyl 4-[(1S)-1-[4-[(1S)-1-[(1-ethyl-2-oxo-4H-pyrimido[4,5-d][1,3]oxazin-7-yl)amino]ethyl]phenyl]-3-methoxy-propyl]piperazine-1-carboxylate (1.372 g, 2.473 mmol) is dissolved in DCM (15 mL) and TFA (10 mL, 15.08 g, 132.3 mmol) is added. The reaction is stirred for 1 hour and then concentrated to dryness. The crude material is dissolved in DCM (12 mL) and DIPEA (1.25 mL, 7.17 mmol) and the mixture is cooled to −78 degrees. Acryloyl chloride (0.18 mL, 0.20 g, 2.2 mmol) is added dropwise. After 10 minutes, a few drops of methanol are added to quench the remaining acryloyl chloride and the reaction is concentrated to dryness (cold). The crude material is chromatographed over silica gel eluting with a gradient of 50-70% acetone in hexanes to give the title compound as a white foam (867 mg, 73%). MS (m/z): 509 (M+H)

The following compound is prepared essentially by the method of Example 13.

TABLE 13

| Ex. No. | Chemical name | Structure | ES/MS (m/z) (M + H) |
|---|---|---|---|
| 14 | 1-Ethyl-7-[[(1S)-1-[4-[3-methoxy-1-(4-prop-2-enoylpiperazin-1-yl)propyl]phenyl]ethyl]amino]-4H-pyrimido[4,5-d][1,3]oxazin-2-one, diastereomer 2 | Chiral | 509 |

EXAMPLE 15

7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one disulfate

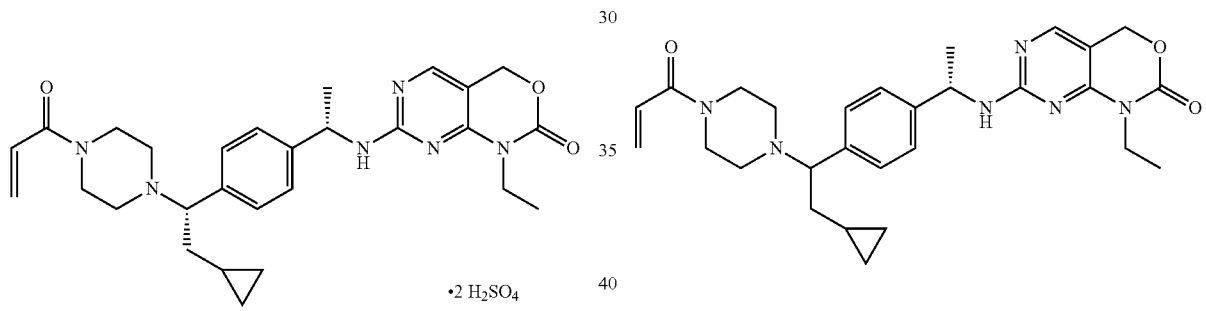

7-[[(1S)-1-[4-[(1S)-2-Cyclopropyl-1-(4-prop-2-enoylpiperazin-1-yl)ethyl]phenyl]ethyl]amino]-1-ethyl-4H-pyrimido[4,5-d][1,3]oxazin-2-one (188 mg) is placed in 5 mL of acetone while stirring at 1000 rpm/60° C. The sample is a clear solution. 45 µL of Sulfuric acid is added dropwise (diluted into 2 mL of acetone). A thick white slurry results after a few drops. After addition of half of the sulfuric acid, the slurry consistency is changed. Addition of the second half of the sulfuric acid is done slowly, dropwise. The slurry gumms slightly before converting to a bright white free-flowing slurry of solid. Heat is shut off to the plate after 30 minutes, and the sample cooled to room temperature, giving a thick slurry of white solid. The white solid is isolated by vacuum filtration. The resulting cake is bright white solid. The sample is dried in place on the filter under air stream for 20 minutes, then in the 70° C. vacuum oven overnight. 266 mg recovered (96.9% yield).

EXAMPLE 16

7-[[(1S)-1-[4-[2-Cyclopropyl-1-(4-prop-2-enoylpiperazin-1-yl)ethyl]phenyl]ethyl]amino]-1-ethyl-4H-pyrimido[4,5-d][1,3]oxazin-2-one 4-hydroxybenzoic acid)

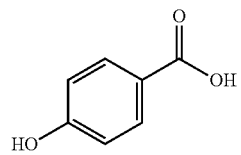

4-Hydroxybenzoic acid (0.023 g, 0.165 mmol) is added to a solution of 7-[[(1S)-1-[4-[2-cyclopropyl-1-(4-prop-2-enoylpiperazin-1-yl)ethyl]phenyl]ethyl]amino]-1-ethyl-4H-pyrimido[4,5-d][1,3]oxazin-2-one (84 mg, 0.165 mmol) in dichloromethane (5 ml). After stirring 5 minutes, the solvent is slowly evaporated under a flow of nitrogen. The resulting solid is further dried under vacuum to give 7-[[(1S)-1-[4-[2-cyclopropyl-1-(4-prop-2-enoylpiperazin-1-yl)ethyl]phenyl]ethyl]amino]-1-ethyl-4H-pyrimido[4,5-d][1,3]oxazin-2-one 4-hydroxybenzoate (105 mg, 0.1617 mmol) as a white solid. MS (m/z): 423.2 (M+H).

PREPARATION 57

2-Cyclopropyl-N-methoxy-N-methylacetamide

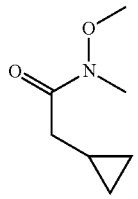

To a stirred 500 mL round bottom flask is charged dichloromethane (160 mL, 8 volumes) and 1,1'-carbonyldiimidazole (35.63 g, 1.1 equiv.). The heterogeneous mixture is cooled to 15° C. and to the mixture is charged a solution of 2-cyclopropylacetic acid (20.0 g, 1.0 equiv.) in dichloromethane (40 mL, 2 volumes) at a rate controlling the internal temperature below 20° C. The resulting solution is warmed to 25° C. and stirred for 2 hours. The solution is then cooled to 15° C. and to it is charged N,O-dimethyl hydroxylamine hydrochloride (21.43 g, 1.1 equiv.) in portions, maintaining the internal temperature below 20° C. The resulting heterogeneous mixture is warmed to 25° C. and stirred for 15 hours. The reaction mixture is then diluted with water (160 mL, 8 volumes) and stirred for 15 minutes. The stirring is stopped and the lower aqueous layer is separated. The resulting aqueous layer is extracted with dichloromethane two more times (100 mL, 5 volumes×2) and the organic layers are combined. The combined organic layer is washed twice with 1.5 N HCl (100 mL, 5 volumes×2). The organic layer is then washed twice with 10% aqueous sodium bicarbonate (100 mL, 5 volumes×2). The organic layer is then washed with water (100 mL, 5 volumes) followed by saturated aqueous sodium chloride (100 mL, 5 volumes). The organic layer is dried over anhydrous sodium sulfate (1.0% w/w). The mass is filtered and washed with dichloromethane (20 mL, 1 volume) and then concentrated under vacuum. The resulting solid is dried under high vacuum for 5 hours to obtain the title compound (25.9 g, 90.5% yield). ES/MS m/z 144.1 (M+H).

ALTERNATIVE SYNTHESIS OF PREPARATION 6

(S)-N-(1-(4-bromophenyl)ethyl)-2,2,2-trifluoroacetamide

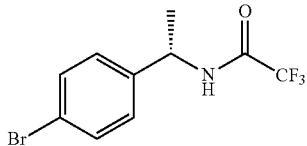

To a stirred 250 mL round bottom flask is charged dichloromethane (100 mL, 10 volumes) followed by (S)-(−)-1-(4-bromophenyl)ethylamine (10.0 g, 1.0 equiv.). The solution is cooled to 0° C. and to the cooled solution is slowly charged trifluoroacetic anhydride (13.12 g, 1.25 equiv.), keeping the internal temperature below 5° C. The resulting heterogeneous mixture is stirred at 0° C. for 2 hours at which time trimethylamine (12.64 g, 2.5 equiv.) is slowly charged, keeping the internal temperature below 5° C. The mixture is stirred for an additional hour and then quenched by the addition of water (30 mL, 3 volumes). The biphasic mixture is warmed to 25° C. and stirred for 30 minutes. The layers are then separated and the aqueous layer is further extracted twice with dichloromethane (50 mL, 5 volumes×2). The combined organic layers are washed with saturated aqueous sodium chloride (50 mL, 5 volumes) and dried over anhydrous sodium sulfate (1 wt %). The dried solution is filtered and washed with dichloromethane (10 mL, 1 volume) and the solution is concentrated under vacuum to give a crude white solid. The crude solid is slurried in petroleum ether (100 mL, 10 volumes for 2 hours at 25° C. and the solid is collected by filtration. The wet solid is dried under vacuum at 40° C. for 8 hours to obtain the title compound (13.3 g, 90% yield). ES/MS m/z 295.3 (M+H).

PREPARATION 58

(S)-N-(1-(4-(2-cyclopropylacetyl)phenyl)ethyl)-2,2,2-trifluoroacetamide

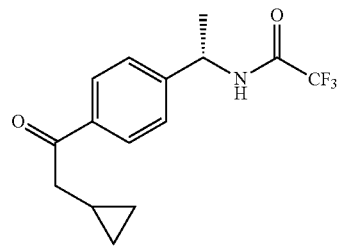 [SMILES: C[C@H](NC(=O)C(F)(F)F)c1ccc(C(=O)CC2CC2)cc1]

To a 10 L reaction vessel with overhead stirring is charged methyl tert-butyl ether (1500 mL, 15 volumes). To the stirred solution is charged (S)-N-(1-(4-bromophenyl)ethyl)-2,2,2-trifluoroacetamide (100 g, 1.0 equiv.). The heterogeneous mixture is stirred at 25° C. for 30 minutes and then is charged tetrahydrofuran (500 mL, 5 volumes). The resulting homogeneous solution is cooled to −83° C. n-Butyl lithium (297 mL, 2.2 equiv.) is slowly added to the solution maintaining the temperature below −78° C. and the resulting solution is stirred at −83° C. for 1.5 hours. To the cooled solution is added a solution of 2-cyclopropyl-N-methoxy-N-methylacetamide (53.19 g, 1.1 equiv.) in methyl tert-butyl ether (200 mL, 2 volumes), maintaining the internal temperature below −78° C. The resulting solution is stirred at −83° C. for 1.5 hours, at which time the solution is warmed to −30° C. and quenched by the addition of saturated aqueous ammonium chloride (5 L, 5 volumes). The quenched reaction mixture is warmed to 25° C. and the layers are separated. The aqueous layer is extracted with methyl tert-butyl ether (500 mL, 5 volumes). The combined organic layers are washed with water (500 mL, 5 volumes), followed by saturated aqueous sodium chloride (500 mL, 5 volumes) and then dried over anhydrous sodium sulfate (50 g, 0.5% w/w). The mass is filtered and washed with methyl tert-butyl ether (50 mL, 0.5 volumes). The resulting solution is concentrated under vacuum until approximately 1 volume of solution remained. Petroleum ether (1500 mL, 15 volumes) is charged to the concentrated mixture and the resulting slurry is stirred below 30° C. for 2 hours. The solid is

PREPARATION 59

N-((S)-1-(4-((S)-2-cyclopropyl-1-hydroxyethyl)phenyl)ethyl)-2,2,2-trifluoroacetamide

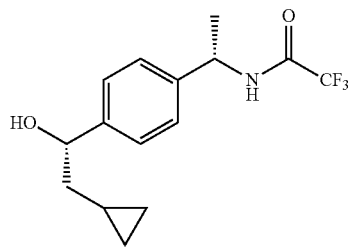 [SMILES: C[C@H](NC(=O)C(F)(F)F)c1ccc([C@@H](O)CC2CC2)cc1]

To a hydrogenator reactor is charged absolute ethanol (7.89 kg, 10 volumes). To the stirred solution is charged (S)-N-(1-(4-(2-cyclopropylacetyl)phenyethyl)-2,2,2-trifluoroacetamide (1.0 kg, 1.0 equiv.). To the solution is charged a solution of potassium tert-butoxide (1.0 M in tBuOH, 0.41 kg, 0.5 volumes) maintaining the internal temperature below 30° C. To the solution is then charged (R)-RUCY®-XylBINAP (0.0675 kg, 0.017 equiv.). The hydrogenator is purged with hydrogen gas twice, while stirring at 25° C. After the purge, the solution is stirred under 4.5 kg of hydrogen pressure at 25° C. for 5 hours. After 5 hours, the solution is vented and then concentrated to an oil with vacuum under 42° C. The oil is dissolved in methyl tert-butyl ether (11.115 kg, 15 volumes) and then concentrated to an oil with vacuum under 45° C. The oil is dissolved in methyl tert-butyl ether (11.115 kg, 15 volumes) and then concentrated to an oil with vacuum under 45° C. To the oil is charged methyl tert-butyl ether (22.23 kg, 30 volumes) at 25° C. The resulting solution is washed with water (15.0 kg, 15 volumes) followed by a NaCl solution in water (5.4 kg NaCl in 15.0 L water). The organic layer is dried over anhydrous sodium sulfate (1.5 kg, 1.5 w/w) and then filtered and washed with methyl tert-butyl ether (1.112 kg, 1.5 volumes). To the filtered solution is charged activated charcoal (0.3 kg, 0.3 w/w) and the mixture is stirred and heated at 40° C. for 2 hours. The mixture is then filtered and washed with methyl tert-butyl ether (1.112 kg, 1.5 volumes). The filtered solution is concentrated to an oil with vacuum under 45° C. The oil is dissolved in petroleum ether (9.84 kg, 15 volumes) and concentrated to an oil with vacuum under 45° C. The oil is dissolved in petroleum ether (9.84 kg, 15 volumes) and concentrated to an oil with vacuum under 45° C. To the oil is charged petroleum ether (19.68 kg, 30 volumes) and the mixture is stirred at 30° C. for 3 hours and the resulting solid is collected by filtration and washed with petroleum ether (9.84 kg, 15 volumes). The isolated solid is dried under vacuum at 40° C. for 5 hours to obtain the title compound (0.79 kg, 79%). ES/MS m/z 300.0 (M−H).

PREPARATION 60

N-((S)-1-(4-((R)-1-chloro-2-cyclopropylethyl)phenyl)ethyl)-2,2,2-trifluoroacetamide

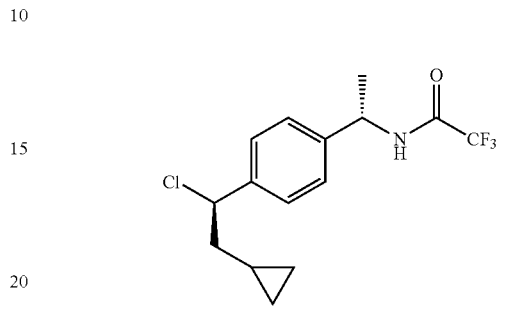

To a reactor is charged methyl tert-butyl ether (4.45 kg, 6 volumes) and N-((S)-1-(4-((S)-2-cyclopropyl-1-hydroxyethyl)phenyl)ethyl)-2,2,2-trifluoroacetamide (1.0 kg, 1.0 equiv.). The solution is cooled to 10° C. and to it is slowly charged 1-formylpyrrolidine (0.066 kg, 0.2 equiv.) maintaining the internal temperature below 13° C. To the solution is then slowly charged benzoyl chloride (0.56 kg, 1.2 equiv.) maintaining the internal temperature below 13° C. The resulting solution is warmed to 25° C. and stirred for up to 36 hours (reaction can be monitored during the course of reaction and if it stalls out, additional charges of 1-formylpyrrolidine and benzoyl chloride can be made). The completed reaction is then concentrated to an oil with vacuum under 40° C. The oil is cooled to 15° C. and then quenched with an aqueous 10% sodium bicarbonate solution (22.0 kg, 20 volumes) and stirred for 3 hours at 25° C. To the biphasic mixture is charged petroleum ether (6.56 kg, 10 volumes). The organic layer is separated. The aqueous layer is extracted with petroleum ether (6.56 kg, 10 volumes). The combined organic layers are washed with aqueous 10% sodium bicarbonate (5.0 L, 5 volumes) three times. The organic layer is then washed with water (5.0 L, 5 volumes) followed by brine (5.0 L, 5 volumes). The organic layer is dried over anhydrous sodium sulfate (0.5 kg, 0.5 w/w). The mixture is then filtered and washed with petroleum ether (0.33 kg, 0.5 volumes). The filtrate is concentrated to an oil with vacuum under 40° C. The oil is dissolved in acetonitrile (3.93 kg, 5 volumes) and concentrated to an oil with vacuum under 40° C. The oil is dissolved in acetonitrile (3.93 kg, 5 volumes) and concentrated to an oil with vacuum under 40° C. The oil is dissolved in acetonitrile (7.86 kg, 10 volumes) and the obtained solution of the title compound is used crude in the next step. ES/MS m/z 318.0 (M−H).

collected by filtration and dried under vacuum at 40° C. for 8 hours to obtain the title compound (65.9 g, 67% yield). ES/MS m/z 298.0 (M−H).

PREPARATION 61 tert-Butyl 4-((S)-2-cyclopropyl-1-(4-((S)-1-(2,2,2-trifluoroacetamido)ethyl)phenyl)ethylpiperazine-1-carboxylate

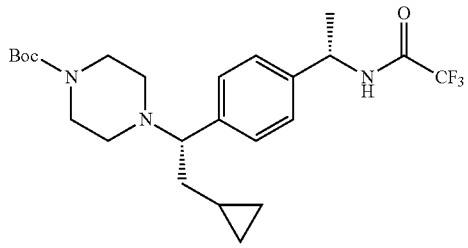 [SMILES: C[C@H](NC(=O)C(F)(F)F)c1ccc([C@H](CC2CC2)N2CCN(C(=O)OC(C)(C)C)CC2)cc1]

To the previously obtained solution of N-(S)-1-(4-((R)-1-chloro-2-cyclopropylethyl)phenyl)ethyl)-2,2,2-trifluoroacetamide is charged N-Boc-piperazine (0.924 kg, 1.5 equiv.) followed by sodium bicarbonate (1.1 kg, 4.0 equiv.). The resulting mixture is heated to 85° C. for 60 hours. Note: the reaction is sampled every 24 hours and after each sample is taken, the reaction is charged with an additional amount of N-Boc-piperazine (0.31 kg, 0.5 equiv.). Once complete, the reaction is concentrated with vacuum under 45° C. to afford an oil. The oil is diluted with water (10.0 kg, 10 volumes) and methyl tert-butyl ether (7.41 kg, 10 volumes). The resulting biphasic mixture is separated and the aqueous layer is extracted with methyl tert-butyl ether (7.41 kg, 10 volumes). The combined organic layers are extracted with 30% citric acid (5.0 L, 5 volumes) five times. The combined aqueous layers are washed twice with petroleum ether (6.56 kg, 10 volumes). The aqueous layer is brought to a pH of 9 with the addition of sodium carbonate (approximately 25.0 kg, 25 w/w) at 15° C. The basified aqueous layer is extracted with methyl tert-butyl ether (7.41 kg, 10 volumes). The combined organic layers are washed with water (5.0 L, 5 volumes) and brine (5.0 L, 5 volumes). The organic layer is dried over anhydrous sodium sulfate (0.5 kg, 50% w/w). The mixture is filtered and washed with methyl tert-butyl ether (0.37 kg, 0.5 volumes). The filtrate is concentrated to an oil by vacuum under 40° C. The resultant oil is dissolved in absolute ethanol (3.95 kg, 5 volumes) and the crude solution of the title compound is used directly in the next step. ES/MS m/z 374.3 (M+H−CF$_3$CO).

PREPARATION 62 tert-Butyl 4-((S)-1-(4-((S)-1-aminoethyl)phenyl)-2-cyclopropylethyl)piperazine-1-carboxylate

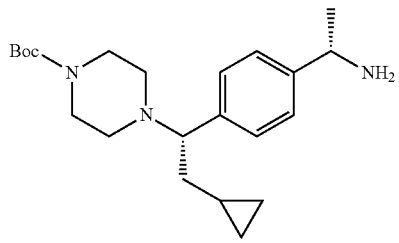 [SMILES: C[C@H](N)c1ccc([C@H](CC2CC2)N2CCN(C(=O)OC(C)(C)C)CC2)cc1]

To the previously obtained solution of tert-butyl 4-((S)-2-cyclopropyl-1-(4-((S)-1-(2,2,2-trifluoroacetamido)ethyl)phenyl)ethylpiperazine-1-carboxylate is charged absolute ethanol (3.7 kg, 3.7 w/w). The solution is cooled to 20° C. and to it is charged aqueous 1 M potassium hydroxide (0.168 kg KOH in 3.0 kg water). The resulting mixture is stirred at 25° C. for 10 hours and then quenched by the slow addition of 30% aqueous citric acid (5.0 kg, 5 w/w) keeping the internal temperature below 30° C. To the quenched solution is charged methyl tert-butyl ether (7.41 kg, 7.41 w/w). The layers are separated and the organic layer is extracted with 30% aqueous citric acid (5.0 kg, 5 w/w). The aqueous layer is brought to a pH of 8 with the addition of sodium carbonate (approximately 25.0 kg, 25 w/w) at 15° C. The basified aqueous layer is extracted twice with ethyl acetate (7.41 kg, 7.41 w/w). The combined organic layers are washed with water (5.0 kg, 5 w/w) and then brine (5.0 kg, 5 w/w). The organic layer is dried over anhydrous sodium sulfate (0.5 kg, 50 wt %), then filtered and washed with ethyl acetate (0.37 kg, 0.37 w/w). The solution is concentrated to an oil by vacuum under 45° C. The resulting oil is dissolved in isopropyl alcohol (2 L, 2 volumes), and the resulting solution is concentrated to an oil by vacuum under 45° C. The resulting oil is dissolved in isopropyl alcohol (1.2 L, 1.2 volumes) and the crude solution of the title compound is used directly in the next purification step. ES/MS m/z 374.2 (M+H).

To a 1000 mL round bottom flask is charged a solution of tert-butyl 4-((S)-1-(4-((S)-1-aminoethyl)phenyl)-2-cyclopropylethyl)piperazine-1-carboxylate (30.0 g, 1.0 equiv.) in isopropyl alcohol (270 mL, 9 volumes). To the stirred solution at 20-30° C. is charged L-dibenzoyl tartaric acid (L-DBTA, 34.5 g, 1.2 equiv.). The solution is stirred at 20-30° C. for 2-4 hours. The resulting slurry is allowed to stir over 8-12 hours at 20-30° C. To the light slurry is charged MTBE (300 mL, 10 volumes). The resulting slurry is allowed to stir and thicken at 20-30° C. over 12-16 hours. The solid is then collected by filtration and washed with MTBE (150 mL, 5 volumes). The solid is dried under reduced pressure at 45-55° C. for 12 hours to afford tert-butyl 4-((S)-1-(4-((S)-1-aminoethyl)phenyl)-2-cyclopropylethyl)piperazine-1-carboxylate L-dibenzoyl tartaric acid salt as a white solid (48.8 g, 83% yield, >98:2 dr).

To a stirred 1000 mL round bottom flask is charged tert-butyl 4-((S)-1-(4-((S)-1-aminoethyl)phenyl)-2-cyclopropylethyl)piperazine-1-carboxylate L-dibenzoyl tartaric acid salt (40.0 g, 1.0 equiv.) followed by dichloromethane (400 mL, 10 volumes). To the stirred solution at 15-25° C. is charged an aqueous solution of 10% Na$_2$CO$_3$ (enough to bring pH to 8-10, approximately 6-8 volumes). The biphasic mixture is stirred for 1 hour at 15-25° C. and then the layers are separated in a separatory funnel. To the organic layer is charged DMSO (240 mL, 6 volumes). The solution is concentrated under reduced pressure below 40° C. to remove the dichloromethane. The solution of freebased tert-butyl 4-((S)-1-(4-((S)-1-aminoethyl)phenyl)-2-cyclopropylethyl)piperazine-1-carboxylate in DMSO is then used directly in the next step.

PREPARATION 63

Ethyl 6-chloro-4-(methylamino)pyridine-3-carboxylate

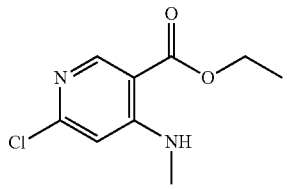

Methyl amine (16 mL, 11.6 mol/L in water, 186 mmol) is added dropwise to a solution of ethyl 4,6-dichloropyridine-3-carboxylate (20 g, 92 mmol) in acetonitrile (300 mL) at 0° C. The reaction mixture is allowed to warm to room temperature over 2 hr. To the reaction mixture is added water and ethyl acetate and the aqueous layer is extracted with ethyl acetate. The combined organic extracts are dried over anhydrous $Na_2SO_4$, filtered, and concentrated to dryness. The resultant crude material is purified by silica gel chromatography (0-100% EtOAc/hexanes) to give, after concentration of the appropriate fractions, ethyl 6-chloro-4-(methylamino)pyridine-3-carboxyl ate as a white solid (10.46 g, 52.14 mmol, 57% yield). MS (m/z): 201 (M+H).

PREPARATION 64

[6-Chloro-4-(methylamino)-3-pyridyl]methanol

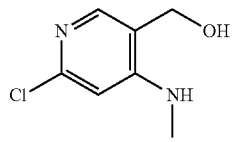

A solution of ethyl 6-chloro-4-(methylamino)pyridine-3-carboxylate (10.46 g, 52.14 mmol) in THF (100 mL) is added dropwise to a mixture of lithium aluminum hydride (78.2 mL, 1.0 mol/L in THF, 78.2 mmol) at 0° C. The reaction mixture is allowed to warm to room temperature over 1.5 hr. To the reaction mixture is added, sequentially, water (3 mL), 15% aqueous NaOH (3 ml), and then water (9 mL). After stirring, the reaction mixture is filtered through a pad of Celite. The filtrate is diluted with water and extracted with dichloromethane. The combined organic extracts are dried over anhydrous $Na_2SO_4$, filtered, and concentrated to dryness to afford [6-chloro-4-(methylamino)-3-pyridyl]methanol as a pale yellow solid (2.78 g, 27% yield). The Celite filter cake is further washed with methanol and the filtrate is concentrated to dryness. The solids from the filter cake are collected and stirred with dichloromethane and filtered through Celite. The filtrate is combined with the residue from the methanol washes and the material is concentrated to dryness and the material is reserved. To the collected solids from the filtration is added 4:1 chloroform:isopropyl alcohol and the mixture is stirred overnight. The mixture is filtered over a pad of Celite, the filtrate is combined with the reserved residue and concentrated to dryness to afford an additional amount of [6-chloro-4-(methylamino)-3-pyridyl]methanol as a pale yellow solid (5.07 g, 56% yield). The total recovery of [6-chloro-4-(methylamino)-3-pyridyl]methanol is 7.85 g, 83% yield). MS (m/z): 173 (M+H).

PREPARATION 65

7-Chloro-1-methyl-4H-pyrido[4,3-d][1,3]oxazin-2-one

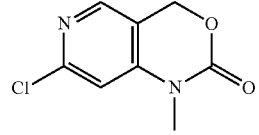

Triphosgene (6.04 g, 20.4 mol) is added to a solution of [6-chloro-4-(methylamino)-3-pyridyl]methanol (5.07 g, 29.1 mol) and DIPEA (51.2 mL, 291 mmol) in THF (100 mL) at −20° C. The cold bath is removed and the mixture is allowed to warm to room temperature. After 30 minutes, water is added and the mixture is extracted with dichloromethane. The combined organic extracts are dried over anhydrous $Na_2SO_4$, filtered, and concentrated to dryness. The resultant crude material is purified by silica gel chromatography (0-100% EtOAc/hexanes) to give, after concentration of the appropriate fractions, 7-chloro-1-methyl-4H-pyrido[4,3-d][1,3]oxazin-2-one as an orange solid (5.13 g, 24.5 mmol, 84% yield). MS (m/z): 199 (M+H).

PREPARATION 66 tert-Butyl 4-[2-cyclopropyl-1-[4-[(1S)-1-[(1-methyl-2-oxo-4H-pyrido[4,3-d][1,3]oxazin-7-yl)amino]ethyl]phenyl]ethyl]piperazine-1-carboxylate, diastereomer 1

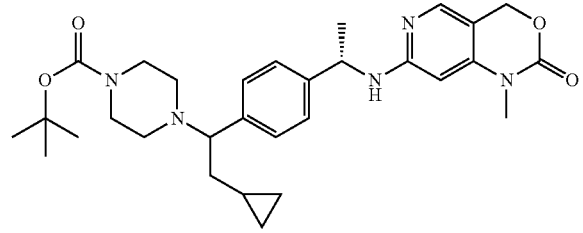 [SMILES: C[C@H](Nc1cc2c(cn1)COC(=O)N2C)c1ccc(C(CC2CC2)N2CCN(C(=O)OC(C)(C)C)CC2)cc1]

To a solution of tert-butyl 4-[1-[4-[(1S)-1-aminoethyl]phenyl]-2-cyclopropyl-ethyl]piperazine-1-carboxylate (1.30 g, 3.48 mmol), 7-chloro-1-methyl-4H-pyrido[4,3-d][1,3]oxazin-2-one (864 mgs, 4.35 mmol), and cesium carbonate (2.27 g, 6.96 mmol) in toluene (17.4 mL) under nitrogen is added dichloro[1,3-bis(2,6-di-3-pentylphenyl)imidazole-2-ylidene](3-chloropyridyl)palladium(II) (291 mgs, 0.348 mmol) and the mixture is heated at 75° C. overnight. After cooling to room temperature, the mixture is filtered through a plug of slica gel and eluted with ethyl acetate. The filtrate is concentrated under reduced pressure and the acquired residue is purified by silica gel chromatography (20-100% EtOAc/hexanes). Mixed fractions are repurified by silica gel chromatography (50-100% methyl tert-butyl ether/hexanes) and the combined pure fractions from both columns are concentrated to give tert-butyl 4-[2-cyclopropyl-1-[4-[(1S)-

1-[(1-methyl-2-oxo-4H-pyrido[4,3-d][1,3]oxazin-7-yl)amino]ethyl]phenyl]ethyl]piperazine-1-carboxylate, diastereomer 1 as an off-white foam (1.312 g, 2.400 mmol, 69% yield). MS (m/z): 536 (M+).

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site). The Wellcome Trust Sanger Institute Cancer Genome Project maintains a detailed online "Cancer Gene Census" of all human genes that have been causally linked to tumorigenesis as well as the COSMIC (Catalogue of Somatic Mutations in Cancer) database of somatic mutations in human cancer. A further source containing abundant information on cytogenetic changes causally linked to various cancers is the Atlas of Genetics and Cytogenetics in Oncology and Haematology.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

Mutations in IDH1 and IDH2 have been identified in multiple cancer tumor types including, but not limited to, glioma, glioblastoma multiforme, astrocytomas, oligodendrogliomas, paraganglioma, myelodysplastic syndrome (MDS), B cell acute lymphoblastic leukemia (B-ALL), thyroid, colorectal, acute myeloid leukemia (AML), Dang et al., *Trends Mol. Med.*, 2010, 16: 387-397; Ward et al., *Oncogene*, 2012, 31(19): 2491-2498; melanoma, Shibata et al., *Am. J. Pathol.*, 2010, 178(3): 1395-1402; prostate, Flaherty et al., *J. Clin. Oncol.*, 2014, 32 (suppl. 4; Abstract 213); Cairns et al., *Cancer Discovery*, 2013, 3: 730-741; chondrosarcoma and cholangiocarcinoma, Balss et al., *Acta Neuropathol.*, 2012, 124: 883-891; Cairns et al., *Cancer Discovery*, 2013, 3: 730-741; angioimmunoblastic T-cell lymphoma (AITL), Cairns et al. *Blood,* 2012. 119(8):1901-1903. Mutations have been found at or near particular residues in the active site: G97D, R100, R132H, R132C, R132S, R132V, R132G, V71I, R132L, and G123R for IDH1, Dang et al., *Trends Mol. Med.*, 2010, 16: 387-397; Ward et al., 2012 and Supplementary Table 2.

Mutant forms of IDH1 and IDH2 have been shown to have a neomorphic activity (gain of function) reducing α-ketoglutarate to 2-hydroxyglutarate. Endogenous production of 2-hydroxyglutarate is enantiospecific resulting in the generation of the D-enantiomer (also termed the (R) enantiomer. Normally, cells have low levels of 2-hydroxyglutarate while cells harboring IDH1 or IDH2 mutations evidence significantly elevated levels of 2-hydroxyglutarate. Significantly elevated levels of 2-hydroxyglutarate are detected in tumors harboring the mutations and in plasma of patients with mutant IDH1 or IDH2. High levels of 2-hydroxyglutarate are associated with a hypermethylation phenotype resulting in a block in differentiation that leads to enhanced tumorigenesis.

The activity of a specific irreversible covalent inhibitor is defined by its binding to the target (IDH1 or IDH2), defined by $K_I$, and the maximum potential rate of covalent bond formation, defined by $k_{inact}$. These two factors are not separate entities, but rather work together to produce the desired effect of covalent bond formation. This is illustrated by the following 3 points.

First, the fact that an electrophile for example, acrylamide, must be properly positioned relative to a nucleophile for example, cysteine, is a fundamental component of covalent bond formation in organic chemistry. There is a precise angle and distance at which the nucleophile must approach the electrophile to form the covalent bond. The simple placement of an electrophile near a nucleophile is not sufficient for covalent bond formation.

Second, when incorporating a reactive group on a core that contains hydrogen bonding moieties to stabilize the binding of the inhibitor to the enzyme for example, an orienting core, a skilled artisan must consider how the orienting core binds to the target and positions the electrophile relative to the nucleophile in light of the optimal angle and distance mentioned above. Again, the simple placement of an electrophile near a nucleophile is not sufficient for covalent bond formation. Changes in the orienting core may impact the ability of an inhibitor compound to form a covalent bond.

Third, when the above two points are considered together, the mere presence of an electrophile moiety on an orienting core is not sufficient to suggest a covalent bond will be formed.

The following in vitro and in vivo studies demonstrate the mutant IDH1 and IDH2 protein inhibitory activity and efficacy of the tested compounds of Formula I or Ia against various specific cancer cell lines. These assays are generally recognized by those skilled in the art as indicative of human clinical therapeutic activity. Inhibition of mutant IDH1 or IDH2 neomorphic proteins in the disclosed studies is believed will be effective against further mutant IDH1 and IDH2 neomorphic proteins. Assays evidencing mutant IDH1 or IDH2 inhibitory activity and efficacy may be carried out substantially as follows or by similar assays affording similar data.

The results of the following assays demonstrate that the compounds exemplified and tested are useful as IDH1 and IDH2 mutant inhibitors and may be useful in treating cancers expressing mutant IDH1 or IDH2.

Biochemical Assays for IDH1 and IDH2 Mutant Enzymes

IDH1-R132H, IDH1-R132C, IDH2-R172K and IDH2-R140Q mutant enzymes catalyze the conversion of αKG to 2HG. 2HG is analyzed using in-line solid phase extraction and mass spectrometry. This analysis is carried out in a RapidFire® instrument coupled to a 6460 triple quadrupole mass spectrometer (G6460A Agilent).

IDH1 mutant (R132H and R132C) and IDH2 mutant (R140Q and R172K) proteins containing N-terminal His-tag are expressed in E. coli and purified using nickel affinity chromatography. The enzyme assays are carried out in V-bottom 96 well polypropylene plates containing 100 mM Tris-HCl buffer, 1 mM DTT, 0.005% TRITON™ X-100, 120 mM NaCl. For IDH1 R132H, α-ketoglutarate, NADPH and $MnCl_2$ are included at final concentrations of 300 μM, 2.5 μM and 300 μM respectively. For IDH1 R132C, α-ketoglutarate, NADPH and $MnCl_2$ are included at final concentrations of 100 μM, 10 μM and 100 μM respectively. For IDH2 R172K, α-ketoglutarate, NADPH and $MnCl_2$ are included at final concentrations of 150 μM, 10 μM and 150 μM respectively. For IDH2 R140Q, α-ketoglutarate, NADPH and $MnCl_2$ are included at final concentrations of 3000 μM, 10 μM and 100 μM respectively. Final pH=7.0. Test compound dissolved in DMSO stock is diluted in the reaction mix at a final DMSO concentration of 4%. Compounds are tested in dose-response format. The assay is started by addition of enzyme. Enzymes are used at the following final concentrations: IDH1 R132H, 2 nM; IDH1 R132C, 0.5 nM; IDH2 R172K, 1.2 nM; IDH2 R140Q, 1.2 nM. After 90 minutes the reaction is quenched by adding ACN (50:50) containing 3-hydroxy-1,5-pentanedioic-2,2,3, 4,4-$d_5$ acid (5$d_5$-3HG) as an internal standard for mass spectrometry analysis and quantitation of reaction product. 2-Hydroxyglutarate (2HG) in quenched samples is separated using strong anionic exchange column chromatography (Phenomenex Strata-X-A SecurityGuard) and analyzed by mass spectrometry in a 6460 triple quadrupole mass spectrometer (G6460A Agilent). The 2HG signal detected is transformed into an analyte concentration using a calibration curve generated using known 2HG concentrations. For each compound tested, the % inhibition is calculated using a DMSO control sample as 0% inhibition and a no enzyme control as 100% inhibition. $IC_{50}$ values are obtained from the individual % inhibition values at different compound concentrations using a 4-parameter equation. These calculations are carried out using Activity Base (IDBS) or Screener (Genedata) data analysis programs.

The results of this assay demonstrate that the exemplified and tested compounds inhibit mutant IDH1 activity against IDH1/R132H and IDH1/R132C and inhbit mutant IDH2 activity against IDH2/R140Q and IDH2/R172K.

The following Examples are tested essentially as described above and exhibit activity against mutant IDH1 and mutant IDH2 as shown in Table 14 below.

TABLE 14

| Example # | IDH1/R132H $IC_{50}$ (μM) | IDH1/R132C $IC_{50}$ (μM) | IDH2/R140Q $IC_{50}$ (μM) | IDH2/R172K $IC_{50}$ (μM) |
|---|---|---|---|---|
| 1 | 0.00569 ± 0.000766, n = 3 | 0.00431 ± 0.000895, n = 3 | 0.113 | 0.0328 |
| 2 | 0.00627 ± 0.00127, n = 3 | 0.00371 ± 0.00126, n = 3 | 0.0369 | 0.0115 |
| 3 | 0.0111 ± 0.0035, n = 2 | 0.0156 ± 0.0075, n = 2 | 0.0648 | 0.0156 |
| 4 | 0.0137 ± 0.0030, n = 2 | 0.00869 ± 0.00280, n = 2 | 0.0811 | 0.028 |
| 5 | 0.00276 | 0.00249 | | |
| 6 | 0.00491 | 0.00505 | | |
| 7 | 0.00638 | <0.00508 | 0.0743 | 0.0224 |
| 8 | <0.00508 | <0.00508 | 0.046 | 0.017 |
| 9 | 0.00743 ± 0.00188, n = 2 | 0.0151 ± 0.0024, n = 2 | | |
| 10 | 0.0139 ± 0.0017, n = 2 | 0.0165 ± 0.0019, n = 2 | | |
| 11 | 0.00978 ± 0.00038, n = 2 | 0.0156 ± 0.0034, n = 2 | 0.0543 | 0.02 |
| 12 | 0.0294 ± 0.0331, n = 2 | 0.0.0390 ± 0.0629, n = 2 | 0.134 | 0.0263 |
| 13 | 0.0124 ± 0.0105, n = 2 | 0.0166 ± 0.0055, n = 2 | 0.239 | 0.039 |
| 14 | 0.0190 ± 0.0224, n = 2 | 0.0186 ± 0.0176, n = 2 | 0.746 | 0.162 |

Mean ± standard deviation of the mean.

Biochemical Assays for Wild-Type IDH1 and IDH2 Enzymes

IDH1 and IDH2 enzymes catalyze the conversion of isocitrate to αKG. Wild-type IDH1 (National Center for Biotechnology Information, Accession: NP_001269316.1) and IDH2 (National Center for Biotechnology Information, Accession: EAX02082.1) proteins containing N-terminal His-tag are expressed in E. coli and purified using nickel affinity chromatography. The enzyme assays are carried out in V-bottom 96 well polypropylene plates containing 100 mM Tris-HCl buffer at pH 7.5, 1 mM DTT, 0.005% TRITON™ X-100, 120 mM NaCl. For the IDH1 wild-type assay isocitrate, $NADP^+$ and $MnCl_2$ are included at the concentrations of 85 μM, 50 μM and 20 μM respectively. For the IDH2 wild-type assay isocitrate, $NADP^+$ and $MnCl_2$ are included at the concentrations of 30 μM, 50 μM and 10 μM respectively. Inhibitors dissolved in a DMSO stock solution are diluted in the reaction mixture at a final DMSO concentration of 4%. The enzyme assay is terminated (quenched) by adding ACN (50:50) containing d6-2-ketopentanedioic acid (d6-αKG) as an internal standard for mass spectrometry analysis. Ten microliters of reaction mixture is combined with 100 μL of water, 50 μL of 1 M O-benzylhydroxylamine in pyridine buffer (8.6% pyridine, pH 5), and 50 μL of 1 M N-(3-dimethylaminopropyl)-N-ethylcarbodiimide hydrochloride (EDC) in pyridine buffer. Following derivatization at room temperature for one hour, samples are extracted with 600 μL of EtOAc. Four hundred μL of the upper layer is removed, dried under heated nitrogen and reconstituted with 100 μL of MeOH/water (1:1). Ten μL of derivatized sample is injected onto an LC-MS system consisting of a Shimadzu Prominence 20A HPLC system and a The Thermo Quantum Ultra™ triple quadrupole mass spectrometer. Analytes are separated on a Waters XBridge™ C18 column (2.1×50 mm, 3.5 μm) with a flow rate of 0.6 mL/minute. Mobile phase A is 0.1% formic acid in water and mobile phase B is MeOH. The αKG signal detected is transformed into analyte concentration using a calibration curve generated using known αKG concentrations. For each compound tested, the % inhibition is calculated using a DMSO control sample as 0% inhibition and a no enzyme control as 100% inhibition. $IC_{50}$ values are obtained from the individual % inhibition values at different compound concentrations using a 4-parameter equation. These calculations are carried out using Activity Base (IDBS) or Screener (Genedata) data analysis programs.

The results of this assay demonstrate that the exemplified and tested compounds are less active at inhibiting the IDH1 wild-type enzyme compared to the IDH1 R132H or R132C mutant enzymes and less active at inhibiting the IDH2 wild-type enzyme compared to the IDH2 R140Q or R172K mutant enzymes.

The following Examples in Table 15 are tested essentially as described above and are less active at inhibiting the wild-type enzymes compared to the mutant enzymes.

TABLE 15

| Example # | IDH1 Wild-Type $IC_{50}$ (μM) | IDH2 Wild-Type $IC_{50}$ (μM) |
|---|---|---|
| 1 | 0.0854 ± 0.107, n = 2 | 0.801 ± 0.745, n = 2 |
| 2 | 0.105 ± 0.113, n = 2 | 0.884 ± 0.748, n = 2 |
| 3 | 0.425 | 3.37 |
| 4 | 0.302 | 3.7 |
| 6 | 0.0549 | 0.493 |
| 7 | 0.233 | 1.53 |
| 8 | 0.237 | 1.62 |
| 11 | 0.345 | 2.08 |
| 12 | 0.277 | 3.22 |
| 13 | 0.456 | 7.03 |
| 14 | 0.392 | 7.4 |

IDH1 (R132H) Biochemical Jump Dilution Assay

Lyophilized Example compounds are reconstituted to 10 mM or 100 mM with 100% DMSO and kept at room temperature until tested. IDH1(R132H)-His protein is expressed and purified by methods well known and commonly used by those skilled in the art. The assay reagents included the following: a-ketoglutaric acid (Sigma Cat #K1875), $MnCl_2$—Fisher Scientific Cat #M87-100, NADPH—Sigma-Aldrich Cat #N7505, Tris-HCl (Invitrogen, Cat #15567-027), NaCl (Sigma, S3014), dithiothreitol (Sigma, D5545), and TRITON™ X100 (Peirce, 28314). The NAD(P)H-Glo™ Kit from Promega (G9061).

The assay buffer used throughout contains 100 mM Tris-HCl pH 7.0, 120 mM NaCl, 1 mM DTT, 0.005% TRITON™ X-100, and 2% DMSO (from the addition of test compound). The $IC_{50}$ of each compound is determined by incubating a dose response of compound, prepared on an Echo555, with 1.5 nM IDH1(R132H), 1 mM α-ketoglutarate, 1 mM $MnCl_2$, and 15 μM NADPH in assay buffer. The reaction is incubated for 2 hours at room temperature, then stopped using 6-cyclopropyl-5-(isoquinolin-5-yl)-2-[(3R)-4-(3-methoxypropanoyl)-3-methylpiperazin-1-yl]pyridine-3-carbonitrile (10 μM). NADPH concentrations are measured using the NAD(P)H-Glo™ Kit, as specified by the vendor. The luminescent signal is read on the Envision (Perkin Elmer; 0.1 sec/Luminescense Mirror/Lum700 WL400-700 filter). In the subsequent jump dilution experiment, a compound concentration equivalent to 10× the $IC_{50}$ is pre-incubated with 100 nM IDH1(R132H). The concentration of compound is always greater than or equal to the enzyme concentration. After 2 hours at room temperature, this mixture is diluted 1:100 into a solution containing a-ketoglutarate (10 mM), $MnCl_2$ (10 mM), and NADPH (15 μM). This final enzyme reaction contains 1 nM IDH1 (R132H) and 0.1×[$IC_{50}$]. After a 2 hour incubation at room temperature, the NADPH concentration is measured as specified above using 6-cyclopropyl-5-(isoquinolin-5-yl)-2-[(3R)-4-(3-methoxypropanoyl)-3-methylpiperazin-1-yl]pyridine-3-carbonitrile and the NAD(P)H-Glo™ Kit. Three controls are included: 1) "10× Control" containing 10×$IC_{50}$ compound in the preincubation and enzyme assay except 1 mM α-ketoglutarate, 1 mM $MnCl_2$, and 15 μM NADPH is used in the final assay measuring enzyme activity, 2) "Max Activity Control" containing DMSO in place of compound for both the preincubation and enzyme assay, and 3) "0.1× Control" containing DMSO in place of compound in the preincubation and 0.1×$IC_{50}$ compound in the enzyme assay. A "Min Activity Control" lacking enzyme, but otherwise equivalent to the "Max Activity Control" is included. A second set of Max and Min Activity Controls is performed using 1 mM α-ketoglutarate, 1 mM $MnCl_2$, and 15 μM NADPH. Each assay condition is tested in triplicate and 32 replicates are performed for the Max Activity Control (10 mM) and Min Activity Control (10 mM) while 16 replicates are performed for the Max Activity Control (1 mM) and Min Activity Control (1 mM).

The concentration of NADP (product) produced in each experiment/control is determined using the percent decrease in the observed signal relative to the Min Activity Control, containing 15 μM NADPH. The Min Activity Control (1 mM and 1.0 mM) and the Max Activity Control (1 mM and 10 mM) are averaged and the standard deviation calculated for each. The signal for each jump dilution and for the 0.1× Controls are multiplied by 15 then divided by the average counts for the Min Activity Control (10 mM) wells. This number is subtracted from 15 to calculate NADP (μM Product). The same calculations are used for the 10× Controls but the Min activity controls (1 mM) are used. The μmoles of the product for the Max Activity controls (1 mM and 10 mM) are calculated by multiplying the average counts by 15 then divide by the respective Min Activity Controls (1 mM and 10 mM). The μM NADP for each well is divided by the average Max Activity Control (1 mM or 10 mM) then multiplied by 100 to determine % IDH Activity for the compound jump dilution, 10× Control, and 0.1× Control. A passing compound must show <30% activity for the 10× control—showing that the pre-incubation concentration is sufficient to saturate the enzyme with compound. In addition, the compound must show >70-80% activity for the 0.1× control confirming that there is no inhibition at the 0.1×/diluted compound concentration.

Example compounds are tested essentially as described above and exhibit % recovery data for IDH1/R132H in this assay. Exemplified and tested compounds of the present invention inhibit the enzyme 2 hours after dilution contrary to art compound(s) that did not inhibit the enzyme 2 hours after dilution with the % recovery. Data from this assay demonstrates that the tested compounds of the present invention act in a manner consistent with covalent inhibition of mutant IDH1 since dilution of the inhibitor does not result in recovery of enzyme activity.

Cell-Based Assays for IDH1 Mutant Inhibitors

To test the cellular inhibition of IDH1 mutant R132C, the fibrosarcoma cell line HT1080 (purchased from ATCC) is used. For testing cell-based inhibition of the R132H mutation, the U87MG glioma cell line (ATCC) was stably transfected with a DNA construct expressing the R132H mutant enzyme by methods well known and routinely used by those skilled in the art.

HT1080 Cell Assay

Fifteen thousand cells are plated in poly-D-lys coated 96 well plates (15,000 cells/well) 18-24 hours prior to treatment with compounds. Four hours prior to compound treatment, cells are glutamine-starved by removing normal media and replacing with glutamine-free media. Following starvation, cells are then treated with different concentrations of test compounds (20 µM to 1 nM; or 0.2 µM to 0.01 nM) dissolved in glutamine free media containing DMSO at a final concentration of 0.2%. The initial compound incubation is for 1 hour at 37° C./5% $CO_2$. After 1 hour, glutamine is added to a final 2 mM concentration and the treated cells are then incubated for a further 18 hours at 37° C./5% $CO_2$. Following the 18 hour incubation, intracellular 2HG and αKG are analyzed in cell lysates. Lysates are prepared following removal of media and addition of buffer containing 25 mM Tris-HCl pH 7.5, 150 mM NaCl, 1 mM EDTA, 1 mM EGTA/1% TRITON™-X 100 to the cells. An aliquot of lysate is added to a mix of $d_6$-αKG and $d_5$-3HG as internal standards and the mixture is treated with O-benzylhydroxylamine in the presence of N-(3-dimethylaminopropyl)-N'-ethylcarbodiimide hydrochloride (EDC) and pyridine. Analyte derivatives are then extracted with EtOAc, dried, and then reconstituted with 50% MeOH in $H_2O$. Samples prepared as described are injected into the HPLC to separate 2HG and αKG derivatives (and corresponding internal standards) using a reverse phase chromatography in a C18 column. Analysis of the samples is carried out using a 6460 triple quadrupole mass spectrometer (G6460A Agilent). The 2HG and αKG signals detected are transformed into analyte concentration using the ratio of αKG/$d_6$-αKG and the ratio of 2HG/$d_5$-3HG that is extrapolated within a calibration curve. Percent inhibition for each individual sample is obtained after normalizing calculated 2HG or αKG concentration to maximum and minimum references obtained in the presence and in the absence of glutamine during cell treatment with compounds. $IC_{50}$ values are obtained from individual % inhibition using a sigmoidal dose-response 4-parameter equation. These calculations are carried out automatically using Activity Base (IDBS) or Screener (Genedata) data analysis programs.

The results of this assay demonstrate that the tested Examples in Table 15 inhibit production of 2-hydroxyglutarate, indicating the inhibition of mutant IDH1 R132C in cells in this assay. αKG, a metabolite generated by wild-type IDH1 is not affected by the inhibitors, indicating the compounds are selective for mutant IDH1 over wild type IDH1 in cells in this assay. The resulting $IC_{50}$ values for the following Examples are shown in Table 16. For those assays in which the inhibition curve did not reach 50%, the highest concentration tested is shown (e.g. IC50>20 µM or >0.2 µM).

TABLE 16

| Example # | HT1080 (R132C, 2-hydroxyglutarate) $IC_{50}$ (µM) | HT1080 (R132C, αKG) $IC_{50}$ (µM) |
|---|---|---|
| 1 | 0.000698 ± 0.000352, n = 7 | >20.0 |
| 2 | 0.00128 ± 0.00100, n = 8 | >20.0 |
| 3 | 0.00127 ± 0.00044, n = 2 | >0.200 |
| 4 | 0.00334 ± 0.00140, n = 2 | >0.200 |
| 5 | 0.000623 ± 0.000745, n = 2 | >20.0 |
| 6 | 0.00112 ± 0.00052, n = 4 | 19.2 |
| 7 | 0.000625 ± 0.000182, n = 2 | >0.200 |
| 8 | 0.000775 ± 0.0000981, n = 2 | >0.200 |
| 9 | 0.00275 ± 0.00046, n = 3 | >20.0 |
| 10 | 0.00391 ± 0.00259, n = 3 | >20.0 |
| 11 | 0.00104 ± 0.00050, n = 4 | >20.0 |
| 12 | 0.00272 ± 0.00330, n = 4 | >20.0 |
| 13 | 0.000987 ± 0.000009, n = 2 | >20.0 |
| 14 | 0.00138 ± 0.00015 n = 3 | >20.0 |

Mean ± standard deviation of the mean.

U87MG/IDH1R132H Cell Assay

Cells are plated in poly-D-lys coated 96 well plates (12,000 cells/well) 18-24 hours previous to treatment with compounds. Four hours prior to compound treatment, cells are glutamine-starved by removing normal media and replacing with glutamine-free media. Following starvation, cells are then treated with different concentrations of test compounds (20 µM to 1 nM) dissolved in glutamine free media containing DMSO at a final concentration of 0.2%. The initial compound incubation is for 1 hour at 37° C./5% $CO_2$. After 1 hour, glutamine is added to a final 2 mM concentration and the treated cells are then incubated for a further 18 hours at 37° C./5% $CO_2$. Intracellular 2HG is analyzed in cell lysates obtained after media removal and treatment with lysis buffer (25 mM Tris-HCl pH 7.5, 150 mM NaCl, 1 mM EDTA, 1 mM EGTA/1% TRITON™-X 100). Cell lysates are conserved at −80° C. until processing. For analyte extraction, an aliquot of thawed lysate is transferred to a deep 96-well plate and treated with cold MeOH containing $d_5$-3HG as an internal standard followed by chloroform and $H_2O$ (1:4:3:2). The upper phase is collected after separation and injected in HPLC to separate 2HG (and internal standard) using hydrophilic interaction (HILIC) chromatography coupled to MS/MS detection in a 6460 triple quadrupole mass spectrometer. Percent inhibition for each individual sample is obtained after normalizing calculated 2HG concentration to maximum and minimum references obtained in the presence and in the absence of glutamine during cell treatment with compounds. $IC_{50}$ values are obtained from individual % inhibition using a sigmoidal dose-response 4-parameter equation. These calculations are carried out automatically using Activity Base (IDBS) or Screener (Genedata) data analysis programs.

The following Examples are tested essentially as described above and exhibit inhibition activity against mutant IDH1/R132H in U87MG cells in this assay as shown in Table 17 below.

TABLE 17

| Example # | U87MG (IDH1/R132H 2-hydroxyglutarate IC$_{50}$ (μM) |
| --- | --- |
| 1 | 0.000209 ± 0.000100, n = 6 |
| 2 | 0.000406 ± 0.000375, n = 8 |
| 3 | 0.000426 ± 0.000188, n = 2 |
| 4 | 0.000805 ± 0.000187, n = 2 |
| 5 | 0.000295 ± 0.00200, n = 2 |
| 6 | 0.000379 ± 0.000202, n = 2 |
| 7 | 0.000356 ± 0.000178, n = 2 |
| 8 | 0.000432 ± 0.000016, n = 2 |
| 9 | 0.000388 ± 0.000703, n = 2 |
| 10 | 0.000529 ± 0.000356, n = 2 |
| 11 | 0.000258 ± 0.000209, n = 3 |
| 12 | 0.00135 ± 0.00151, n = 4 |
| 13 | 0.000267 ± 0.000227, n = 2 |
| 14 | 0.000353 ± 0.000483, n = 2 |

Mean ± standard deviation of the mean.

In Vivo 2-Hydroxyglutarate Assay

For in vivo testing of IDH1 inhibitors, sub-cutaneous xenograft tumors are grown in athymic nude mice (20-22 g, Harlan Laboratories) following implantation of either HT1080 cells (fibrosarcoma carrying R132C mutant IDH1) or TB08 cells (secondary glioblastoma carrying R132H mutant IDH1). Mice are fed and watered ad libitum and are acclimatized for 1 week prior to implantation of cells. Tumor cells (HT1080) or tumor fragments (TB08) are implanted into the right rear flank. For HT1080, 5.0×10$^6$ cells are implanted in a 1:1 mixture with Matrigel in a final volume of 0.2 ml. For TB08, tumor fragments generated from ex-planted tumor samples are implanted directly into the hind flank. Tumor volumes are measured by caliper twice weekly and tumor volume is calculated using 0.536×L×W$^2$, where L=length and W=width. When tumor volumes reach 150-400 mm$^3$, animals are randomized, placed into groups (n=3-6 per group) and dosed with IDH1 inhibitors or vehicle control. For IDH1 inhibitors, compounds are formulated in vehicle containing either 1% hydroxyethylcellulose/0.25% Tween™ 80/0.05% Antifoam or 10% Acacia with 1.1 mol equivalent of HCl. Compounds are bath sonicated to obtain suspension. Compounds are dosed on a milligram per kilogram (mpk) basis via oral gavage in a final volume of 0.2 ml. To determine inhibition of 2HG, compounds are dosed twice daily (BID) for 3 days (total number of doses=6). Following compound treatment, mice are euthanized with isofluorane anesthesia and cervical dislocation. Tumors are excised, put into labeled tubes, and immediately frozen in liquid nitrogen. Tumors are stored at −80° C. for processing.

Preparation of Tumor Lysates

XY Lite buffer is prepared in molecular grade water and contains the following components: 25 mM Tris, pH 7.5, 150 mM NaCl, 1% TRITON™ X-100, 1 mM EDTA, 1 mM EGTA. To XY Lite (40 ml), 800 μl of Halt Protease and Phosphatase Inhibitors cocktail (Halt™ Protease and Phosphatase Inhibitor Cocktail, EDTA-Free Thermo Scientific, Cat #78441) is added. Samples are vortexed and then chilled on ice. Orange cap lysing-A tubes are labeled and placed in a rack on ice. A ceramic mortar and pestle is placed in dry ice to cool. A 2×2 inch square of aluminum foil is placed in the bottom of the mortar. A tumor sample is transferred to the pre-chilled mortar on the foil square. Liquid nitrogen (about 5 ml) is added and allowed to evaporate, super-freezing the tumor. Another piece of foil is placed over the tumor and the tumor smashed to small pieces with the ceramic pestle. The crushed tumor is quickly transferred to the lysing tube. Ice-cold XY Lite (500 μL) is added to each tube and capped. Tumors are then processed on the FastPrep-24 MP Biomedicals by spinning twice for 35 seconds each at speed setting 5. Samples are then centrifuged in Beckman Microfuge R at 4° C. at 14,000 rpm for 30 minutes. Supernatant is transferred to a pre-chilled 96 deep well plate. The pellet is discarded.

Protein Assay

A protein assay dilution plate is first generated by adding XY buffer (145 μl) to a non-sterile 96 well round bottom Corning plate. To this, tumor lysate (5 μL) is added and gently mixed. The plate is kept on ice. Serial dilutions of BSA standard (Thermo Scientific cat. 23209 2 mg/mL) are set-up as follows: Five 0.5 mL tubes are placed in a rack and XY buffer (60 μL) is added to each. Stock BSA (60 μl) is added to first tube and vortexed. 60 μl from the first tube is transferred to the next tube, vortexed, and so forth, until the dilution series is complete as follows: Tube 1=stock BSA, Tubes 2-5 are 1:2 serial dilutions, Tube 6=XY buffer alone. Thermo BCA Protein Assay reagents are mixed according to manufacturer instructions. Mixed BCA Reagent (200 μl) is added to each sample and incubated for 15 minutes. The protein assay results are read on SOFTmax Pro Plate Reader. Based on protein assay results, the appropriate amount of XY buffer is added to each tumor lysate to generate a final protein concentration of 5 mg/mL. All samples are labeled and stored at −80° C.

Metabolite Analysis in Tumor Lysates

The in vivo effects of IDH1 inhibition on the concentrations of total 2HG and αKG is determined by liquid chromatography-mass spectrometry (LC-MS) analysis of tumor xenografts. The method utilizes derivatization with O-benzylhydroxylamine prior to analysis by LC-MS. Ten microliters of each tumor lysate is placed into a deep-well 96-well plate and combined with 100 μL of internal standard solution containing 10 μM d$_5$-3HG and 10 μM d$_6$-αKG. 50 μL of 1 M O-benzylhydroxylamine in pyridine buffer (8.6% pyridine, pH 5) and 50 μL of 1 M N-(3-dimethylaminopropyl)-N-ethylcarbodiimide hydrochloride (EDC) in pyridine buffer is added to each sample. The derivatization reaction proceeds at room temperature for one hour. Using a Beckman Biomek FX liquid handler 600 μL of EtOAc is added to each sample. Plates are sealed and vortexed for 5 minutes, then they are centrifuged for 5 minutes at 4000 rpm in Eppendorf 5810R centrifuge. 400 μL of the upper layer is transferred to a new 96-well plate. Samples are dried under heated nitrogen at 50 ° C. and reconstituted with 100 μL of MeOH/water (1:1). One microliter of derivatized sample is injected onto an LC-MS system consisting of a Shimadzu Prominence 20A HPLC system and a Thermo Quantum Ultra™ triple quadrupole mass spectrometer. Analytes are separated on a Water XBridge™ C18 column (2.1×50 mm, 3.5 μm) with a flow rate of 0.6 mL/minute. Mobile phase A is 0.1% formic acid in water and mobile phase B is MeOH. The gradient profile is: 0 minutes, 5% B; 3 minutes, 100% B; 4.00 minutes, 100% B; 4.1 minutes, 5% B; 5.50 minutes, stop. The mass spectrometer utilizes a HESI-II probe operated in positive ion selected reaction monitoring mode. Calibration curves are constructed by plotting analyte concentrations vs. analyte/internal standard peak area ratios and performing a quadratic fit of the data using a 1/concentration weighting with Xcalibur™ software. Analyte concentrations for the unknowns are back-calculated from the calibration curves. Metabolite data from the LC-MS assay is expressed in nmol/mg protein. The average 2HG level in the vehicle treated group is used to determine the 0% inhibition control. The % inhibition in each inhibitor treated animal is then determined relative to the vehicle control. Data are analyzed in JMP software to determine the average % inhibition in each dose group, the standard deviation, and the standard error.

Data demonstrating in vivo inhibition of 2-hydroxyglutarate in IDH1 mutant xenograft mice by exemplified and tested compounds is shown in Table 18 below.

TABLE 18

| Xenograft Model | Treatment or Ex No. | Dose | Mice (n) | 2HG, Mean % Inhibition | Std Dev | Std Err Mean |
|---|---|---|---|---|---|---|
| TB08 (R132H) | Vehicle | 0 mpk | 5 | 0 | 30.3 | 13.55 |
| TB08 (R132H) | 1 | 1 mpk | 5 | 21.4 | 21 | 9.38 |
| TB08 (R132H) | 1 | 2 mpk | 5 | 16.1 | 30.3 | 13.6 |
| TB08 (R132H) | 1 | 4 mpk | 5 | 41.5 | 26 | 11.6 |
| TB08 (R132H) | 1 | 8 mpk | 5 | 78.8 | 1.8 | 0.8 |
| TB08 (R132H) | 1 | 16 mpk | 5 | 92.1 | 1.8 | 0.8 |
| TB08 (R132H) | 1 | 32 mpk | 5 | 95.8 | 0.7 | 0.3 |

| Xenograft Model | Treatment or Ex No. | Dose | Number Mice | 2HG, Mean % Inhibition | Std Dev | Std Err Mean |
|---|---|---|---|---|---|---|
| TB08 (R132H) | Vehicle | 0 mpk | 5 | 0 | 39.2 | 17.5 |
| TB08 (R132H) | 2 | 1 mpk | 5 | 37.4 | 13.3 | 5.9 |
| TB08 (R132H) | 2 | 2 mpk | 5 | 23.9 | 16.2 | 7.2 |
| TB08 (R132H) | 2 | 4 mpk | 5 | 63.7 | 12.1 | 5.4 |
| TB08 (R132H) | 2 | 8 mpk | 5 | 80.95 | 6.27 | 2.8 |
| TB08 (R132H) | 2 | 16 mpk | 5 | 92.97 | 2.63 | 1.1 |
| TB08 (R132H) | 2 | 32 mpk | 5 | 96.88 | 0.68 | 0.3 |
| TB08 (R132H) | Vehicle | 0.00 mpk | 5 | 0 | 24.4 | 10.9 |
| TB08 (R132H) | 8 | 10.0 mpk | 5 | 60.36 | 10.06 | 4.5 |
| TB08 (R132H) | 7 | 10.0 mpk | 5 | 69.56 | 9.15 | 4.1 |
| TB08 (R132H) | 4 | 10.0 mpk | 5 | 61.82 | 14.4 | 6.4 |
| TB08 (R132H) | 3 | 10.0 mpk | 5 | 87.26 | 3.95 | 1.77 |
| TB08 (R132H) | 14 | 10.0 mpk | 5 | 86.71 | 5.27 | 2.36 |
| TB08 (R132H) | Vehicle | 0.00 mpk | 5 | 0 | 26.87 | 12.02 |
| TB08 (R132H) | 11 | 10.0 mpk | 5 | 90.63 | 4.5 | 2.01 |
| TB08 (R132H) | Vehicle | 0.00 mpk | 5 | 0 | 39.6 | 17.7 |
| TB08 (R132H) | 13 | 10.0 mpk | 5 | 86.3 | 3.7 | 1.67 |
| TB08 (R132H) | 12 | 10.0 mpk | 5 | 94.16 | 0.66 | 0.3 |

We claim:

1. A compound of the Formula:

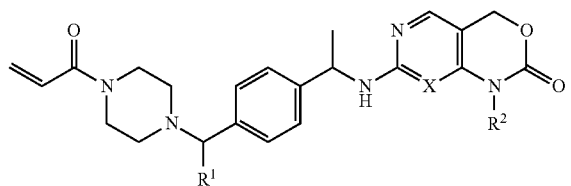

wherein:
$R^1$ is $-CH_2CH(CH_3)_2$, $-CH_2CH_3$, $-CH_2CH_2OCH_3$, or $-CH_2$-cyclopropyl;
$R^2$ is $-CH_3$ or $-CH_2CH_3$;
X is CH; or
a pharmaceutically acceptable salt thereof.

2. A compound of claim 1 which is:
7-[[(1S)-1-[4-[2-Cyclopropyl-1-(4-prop-2-enoylpiperazin-1-yl)ethyl]phenyl]ethyl]amino]-1-methyl-4H-pyrido[4,3-d][1,3]oxazin-2-one, isomer 1;
7-[[(1S)-1-[4-[2-Cyclopropyl-1-(4-prop-2-enoylpiperazin-1-yl)ethyl]phenyl]ethyl]amino]-1-methyl-4H-pyrido[4,3-d][1,3]oxazin-2-one, isomer 2;
or a pharmaceutically acceptable salt thereof.

3. A pharmaceutical composition comprising a compound of claim 1, or a pharmaceutically acceptable salt thereof, and a pharmaceutically acceptable carrier.

* * * * *